United States Patent
Schulhauser et al.

(10) Patent No.: US 11,623,102 B2
(45) Date of Patent: Apr. 11, 2023

(54) WEARABLE DEFIBRILLATION APPARATUS CONFIGURED TO APPLY A MACHINE LEARNING ALGORITHM

(71) Applicant: Medtronic, Inc., Minneapolis, MN (US)

(72) Inventors: Randal C. Schulhauser, Phoenix, AZ (US); Jian Cao, Shoreview, MN (US); David Probst, Chandler, AZ (US); Daniel Hahn, Tempe, AZ (US); Eric C. Maass, Scottsdale, AZ (US); Patrick W. Kinzie, Glendale, AZ (US)

(73) Assignee: MEDTRONIC, INC., Minneapolis, MN (US)

( * ) Notice: Subject to any disclaimer, the term of this patent is extended or adjusted under 35 U.S.C. 154(b) by 249 days.

(21) Appl. No.: 16/050,928

(22) Filed: Jul. 31, 2018

(65) Prior Publication Data
US 2020/0038671 A1 Feb. 6, 2020

(51) Int. Cl.
*A61N 1/39* (2006.01)
*A61B 5/00* (2006.01)
(Continued)

(52) U.S. Cl.
CPC .......... *A61N 1/3904* (2017.08); *A61B 5/0031* (2013.01); *A61B 5/021* (2013.01);
(Continued)

(58) Field of Classification Search
CPC ........... A61B 5/00; A61B 5/04; A61B 5/0408; A61B 5/042; A61B 5/0452; A61B 5/7275;
(Continued)

(56) References Cited

U.S. PATENT DOCUMENTS

| | | | |
|---|---|---|---|
| 4,458,691 | A | 7/1984 | Netravali |
| 6,065,154 | A | 5/2000 | Hulings et al. |

(Continued)

FOREIGN PATENT DOCUMENTS

| | | |
|---|---|---|
| WO | 2010107913 A2 | 9/2010 |
| WO | 2017035140 A1 | 3/2017 |

OTHER PUBLICATIONS

Oxford Dictionary definition of "preliminary", https://www.oxfordlearnersdictionaries.com/us/definition/english/preliminary_2. printed May 3, 2022.*

(Continued)

*Primary Examiner* — Allen Porter
*Assistant Examiner* — Adreanne A. Arnold
(74) *Attorney, Agent, or Firm* — Shumaker & Sieffert, P.A.

(57) ABSTRACT

In some examples, an apparatus configured to be worn by a patient for cardiac defibrillation comprises sensing electrodes configured to sense a cardiac signal of the patient, defibrillation electrodes, therapy delivery circuitry configured to deliver defibrillation therapy to the patient via the defibrillation electrodes, communication circuitry configured to receive data of at least one physiological signal of the patient from at least one sensing device separate from the apparatus, a memory configured to store the data, the cardiac signal, and a machine learning algorithm, and processing circuitry configured to apply the machine learning algorithm to the data and the cardiac signal to probabilistically-determine at least one state of the patient and determine whether to control delivery of the defibrillation therapy based on the at least one probabilistically-determined patient state.

34 Claims, 29 Drawing Sheets

(51) Int. Cl.

| | | |
|---|---|---|
| *A61B 5/145* | (2006.01) | |
| *A61N 1/04* | (2006.01) | |
| *A61B 5/021* | (2006.01) | |
| *A61B 5/024* | (2006.01) | |
| *A61B 5/08* | (2006.01) | |
| *A61B 5/11* | (2006.01) | |
| *A61B 5/369* | (2021.01) | |

(52) U.S. Cl.
CPC ............... *A61B 5/024* (2013.01); *A61B 5/08* (2013.01); *A61B 5/11* (2013.01); *A61B 5/14532* (2013.01); *A61B 5/14542* (2013.01); *A61B 5/369* (2021.01); *A61B 5/7275* (2013.01); *A61N 1/046* (2013.01)

(58) Field of Classification Search
CPC .... A61B 5/02; A61B 5/08; A61N 1/39; A61N 1/3904
See application file for complete search history.

(56) References Cited

U.S. PATENT DOCUMENTS

| | | | |
|---|---|---|---|
| 6,308,094 B1 | 10/2001 | Shusterman et al. | |
| 7,974,689 B2 | 7/2011 | Volpe et al. | |
| 7,991,467 B2 | 8/2011 | Markowitz et al. | |
| 8,364,260 B2 | 1/2013 | Kumar | |
| 8,369,944 B2 | 2/2013 | Macho et al. | |
| 8,412,317 B2 | 4/2013 | Mazar | |
| 8,532,785 B1 | 9/2013 | Crutchfield et al. | |
| 8,548,584 B2 | 10/2013 | Jorgenson | |
| 8,548,828 B1 | 10/2013 | Longmire | |
| 8,706,215 B2 | 4/2014 | Kaib et al. | |
| 8,774,923 B2 | 7/2014 | Rom | |
| 8,823,490 B2 | 9/2014 | Libbus et al. | |
| 8,864,676 B2 | 10/2014 | Beasley et al. | |
| 8,880,196 B2 | 11/2014 | Kaid | |
| 8,886,314 B2 | 11/2014 | Crutchfield et al. | |
| 8,903,484 B2 | 12/2014 | Mazar | |
| 8,983,597 B2 | 3/2015 | Whiting et al. | |
| 9,089,685 B2 | 7/2015 | Sullivan et al. | |
| 9,101,780 B2 | 8/2015 | Cheng et al. | |
| 9,183,351 B2 | 11/2015 | Shusterman | |
| 9,237,858 B2 | 1/2016 | Krusor et al. | |
| 9,345,898 B2 | 5/2016 | Piha et al. | |
| 9,420,956 B2 | 8/2016 | Gopalakrishnan et al. | |
| 9,445,719 B2 | 9/2016 | Libbus et al. | |
| 9,451,897 B2 | 9/2016 | Mazar et al. | |
| 9,526,910 B2 | 12/2016 | Crutchfield et al. | |
| 9,539,435 B2 | 1/2017 | Rasmussen et al. | |
| 9,585,590 B2 | 3/2017 | McNair | |
| 9,700,227 B2 | 7/2017 | Bishay et al. | |
| 9,757,579 B2 | 9/2017 | Foshee et al. | |
| 9,781,243 B1 | 10/2017 | Huang | |
| 2003/0083559 A1 | 5/2003 | Thompson | |
| 2004/0133242 A1 | 7/2004 | Chapman et al. | |
| 2005/0115561 A1 | 6/2005 | Stahmann et al. | |
| 2006/0173498 A1 | 8/2006 | Banville et al. | |
| 2010/0056881 A1 | 3/2010 | Libbus et al. | |
| 2011/0144470 A1 | 6/2011 | Mazar et al. | |
| 2015/0015417 A1 | 1/2015 | Libbus et al. | |
| 2015/0217121 A1 | 8/2015 | Subramanian et al. | |
| 2015/0265164 A1* | 9/2015 | Gopalakrishnan ..... | G16H 40/67 600/513 |
| 2015/0297904 A1 | 10/2015 | Kavounas | |
| 2015/0328472 A1 | 11/2015 | Sullivan et al. | |
| 2016/0000349 A1* | 1/2016 | Sullivan ............... | A61B 5/7221 600/509 |
| 2016/0007872 A1 | 1/2016 | Bishay et al. | |
| 2016/0067508 A1 | 3/2016 | Boone et al. | |
| 2016/0067513 A1 | 3/2016 | Crutchfield et al. | |
| 2016/0074667 A1 | 3/2016 | Sullivan et al. | |
| 2016/0082277 A1 | 3/2016 | Foshee, Jr. et al. | |
| 2016/0129186 A1 | 5/2016 | Douglas et al. | |
| 2016/0220825 A1 | 8/2016 | Greenhut et al. | |
| 2016/0342753 A1 | 11/2016 | Feazell | |
| 2017/0095673 A1* | 4/2017 | Ludwig .................. | G16H 50/20 |
| 2017/0196458 A1* | 7/2017 | Ternes .................... | A61B 5/686 |
| 2017/0265765 A1* | 9/2017 | Baumann ............... | A61B 5/339 |
| 2017/0372009 A1 | 12/2017 | Sanyal et al. | |
| 2018/0116537 A1 | 5/2018 | Sullivan et al. | |
| 2018/0146929 A1 | 5/2018 | Joo et al. | |
| 2019/0232046 A1* | 8/2019 | Chu ........................ | A61H 23/00 |
| 2019/0329055 A1* | 10/2019 | Briscoe ................ | A61N 1/3925 |
| 2019/0387992 A1* | 12/2019 | May ...................... | A61B 5/341 |

OTHER PUBLICATIONS (PCT/US2019/044092) PCT Notification of Transmittal of the International Search Report and the Written Opinion of the International Searching Authority, dated Nov. 5, 2019, 11 pages.

"LifeVest Patient Education Video Chapter 1: LifeVest Protection from Sudden Cardiac Death," Youtube.com, retrieved from https://www.youtube.com/watch?v=Kj6SK1qmdQw, Aug. 1, 2018, 1 pp.

"This Device Could Save Your Life," Youtube.com, retrieved from https://www.youtube.com/watch?v=BdWikwU5bPY&sns=em, Aug. 1, 2018, 1 pp.

Kelwade et al., "Prediction of Cardiac Arrhythmia using Artificial Neural Network," International Journal of Computer Applications (0975-8887), vol. 115, No. 20, Apr. 2015, pp. 30-35.

Lau et al., "Connecting the Dots: From Big Data to Healthy Heart," Circulation, vol. 134, Aug. 2, 2016, pp. 362-364.

\* cited by examiner

WEARABLE DEFIBRILLATION APPARATUS CONFIGURED TO APPLY A MACHINE LEARNING ALGORITHM

TECHNICAL FIELD

This disclosure relates to medical devices, and more particularly, to cardiac defibrillators.

BACKGROUND

Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Sudden cardiac death (SCD) may result in a matter of minutes.

A wearable automated external defibrillator (WAED), also referred to as a wearable cardiac defibrillator (WCD), is an option for patients having an identified risk of malignant tachyarrhythmia, but for whom an implantable cardioverter-defibrillator is not indicated or desired. WAEDs typically include straps or a garment carrying its components, such as sensing and defibrillation electrodes, processing circuitry, and shock generation and sensing circuitry, which allow such components to be worn by a patient. WAEDs typically implement conventional AED arrhythmia detection algorithms in which seconds of the most recent electrocardiogram data are analyzed, and which do not consider other types of sensor data typically not available to the WAED.

SUMMARY

In some aspects, this disclosure describes examples of systems, devices, and techniques for detection of tachyarrhythmia and, in some cases, cardiac defibrillation. A patient may wear a defibrillation apparatus, such as a WAED. The processing circuitry of the apparatus may implement a machine learning algorithm to probabilistically determine a state of a patient, e.g., to determine a tachyarrhythmia state of the patient as part of is tachyarrhythmia detection algorithm and/or a state of a comorbidity, such as chronic obstructive pulmonary disease (COPD). The processing circuitry of the apparatus may have a graphics processing unit (GPU) and central processing unit (CPU) architecture, which may allow the apparatus to implement the machine learning algorithm.

The machine learning algorithm enables the defibrillation apparatus to implement a probabilistic determination, e.g., using a Bayesian, random forest, and/or decision tree methodology, of whether the patient's condition is normal or not normal, e.g., whether the patient is experiencing or will experience a treatable tachyarrhythmia, which may also be referred to as the tachyarrhythmia state of the patient. The machine learning algorithm and the GPU architecture also enable the apparatus to make the probabilistic determination by considering large amounts of diverse data together, and identifying patterns in the data. The data may include present and historical values of (or values derived from) time-varying signals, such as an electrocardiogram (ECG) and/or other sensed physiological or environmental signals.

In some examples, the apparatus receives data including signals, values, or independent determinations of patient state, for consideration by the GPU according to the machine learning algorithm, from one or more other sensing devices, which may be wearable by or implanted in the patient. The apparatus may be the master for such other sensing devices in a master/slave communication relationship. The probabilistic determination based on a variety of types of data and signal sources may allow a more accurate determination of patient state, particularly when confronted with noise in one or more signals. In some examples, the probabilistic determination may allow prediction of tachyarrhythmia prior to its occurrence, and preventative therapy, such as cardiac pacing or other electrical stimulation to disrupt a cardiac rhythm, rather than defibrillation shock in response to fibrillation.

The apparatus, via the GPU, may update a machine learning algorithm based on the collected data. In some examples, e.g., during an initial training phase with the patient's data, the updates to the machine learning algorithm may also be based on feedback from a user or other device regarding whether the algorithm's determinations of the patient's state were correct. Furthermore, in some examples, a remote system may implement a more extensive GPU architecture, e.g., with a greater number of cores or otherwise with a greater ability to process data and update the algorithm. The remote system may receive the collected data and patient state decisions from the apparatus, update its instance of the algorithm based on the data and decisions, and provide the updates to the apparatus. In some examples, different populations may be distinguished from one another based on different characteristics, and the remote system may use population-specific data to update population-specific machine learning algorithms for patients within each population. Additionally, in cases in which a patient wearing such a defibrillation apparatus is later indicated for implantation of an ICD, the tachyarrhythmia detection algorithm of the ICD may implement or be configured based on the machine learning algorithm stored in the defibrillation apparatus, which has learned to detect tachyarrhythmias of the particular patient over time.

In one example, an apparatus configured to be worn by a patient for cardiac defibrillation comprises sensing electrodes configured to sense a cardiac signal of the patient, defibrillation electrodes, therapy delivery circuitry configured to deliver defibrillation therapy to the patient via the defibrillation electrodes, communication circuitry configured to receive data of at least one physiological signal of the patient from at least one sensing device separate from the apparatus, and a memory configured to store the data, the cardiac signal, and a machine learning algorithm. The apparatus further comprises processing circuitry configured to apply the machine learning algorithm to the data and the cardiac signal to probabilistically determine at least one state of the patient, and determine whether to control delivery of the defibrillation therapy based on the at least one probabilistically-determined state of the patient.

In another example, a method for monitoring cardiac signals and determining whether to deliver defibrillation therapy by apparatus configured to be worn by a patient comprises sensing, via sensing electrodes of the apparatus, a cardiac signal of the patient, receiving, by communication circuitry of the apparatus, data of at least one physiological signal of the patient from at least one sensing device separate from the apparatus, storing, by a memory of the apparatus, the cardiac signal, the data, and a machine learning algorithm, applying, by processing circuitry of the apparatus, the machine learning algorithm to the data and the cardiac signal to probabilistically determine at least one state of the patient, and determining, by the processing circuitry, whether to control delivery of defibrillation therapy by therapy delivery circuitry of the apparatus based on the at least one probabilistically-determined state of the patient.

In another example, a system for cardiac defibrillation comprises an apparatus configured to deliver defibrillation therapy, wherein the apparatus is configured to be worn by a patient, wherein the apparatus comprises processing circuitry comprising a first graphics processing unit (GPU), sensing electrodes configured to sense a cardiac signal of the patient, defibrillation electrodes, therapy delivery circuitry configured to deliver defibrillation therapy to the patient via the defibrillation electrodes, and a memory configured to store the cardiac signal and a machine learning algorithm. The system further comprises a computing system communicatively coupled to the apparatus, the computing system comprising a second GPU, wherein the first GPU is configured to apply the machine learning algorithm to the cardiac signal, and the processing circuitry is configured to determine whether to control delivery of the defibrillation therapy based on a result of the application of the machine learning algorithm to the cardiac signal, and wherein the second GPU is configured to update the machine learning algorithm based on the cardiac signal and population data, wherein the population data comprises data of cardiac signals from a plurality of other patients.

In another example, a system for determining a tachyarrhythmia state of a patient comprises an apparatus configured to be worn by the patient and a sensing device separate from the apparatus. The apparatus comprises sensing electrodes configured to sense a cardiac signal of the patient, communication circuitry configured to receive data of at least one physiological signal of the patient from the sensing device via wireless communication, a memory configured to store the data, the cardiac signal, and a machine learning algorithm, and processing circuitry configured to apply the machine learning algorithm to the data and the cardiac signal to determine the treatable tachyarrhythmia state of the patient. The processing circuitry of the apparatus is configured to request the data as a master from the sensing device as a slave according to a master/slave relationship.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

In some aspects, the techniques described herein include collecting data form one or more sources, applying a machine learning algorithm to the data, determining whether to deliver therapy based on a result of the application of the machine learning algorithm to the data and, if it is determined to deliver therapy, delivering the therapy. The machine learning algorithm may be implemented by a GPU of a defibrillation apparatus, such as a WAED. The machine learning algorithm may be updated based on data of the patient and data from a greater population. The machine learning algorithm may be configured to characterize the patient data as normal or non-normal or otherwise determine one or more states of the patient.

As an example, a patient may wear the vest apparatus (e.g., the WAED) having a GPU and also have an insertable cardiac monitor implanted subcutaneously. Each of these devices may sense a cardiac signal of the heart of the patient. The vest apparatus may control the insertable cardiac monitor to perform various tasks, such as transmit sensed signals to the vest apparatus. In other words, the vest apparatus may act as a master for the insertable cardiac monitor in a master/slave relationship.

Based on the signals, the machine learning algorithm implemented by the GPU of the vest apparatus may determine that the patient has an arrhythmia, and the vest apparatus may be configured to deliver therapy to the patient to treat the arrhythmia. The patient (or a healthcare professional) may confirm, e.g., via a user interface of the vest apparatus or another device, whether an adverse event is in fact occurring. In this way, the patient and/or a healthcare provider, may contribute to the development of the machine learning algorithm, e.g., provide reinforcement in near real-time for reinforced learning by the algorithm. In some examples, the cardiac monitor or another device may make an independent determination of the arrhythmia, which may provide near real-time feedback (reinforcement) for reinforced learning development of the machine learning algorithm. The GPU, based on the preceding events and signals, may update the machine learning algorithm.

Figure 1:
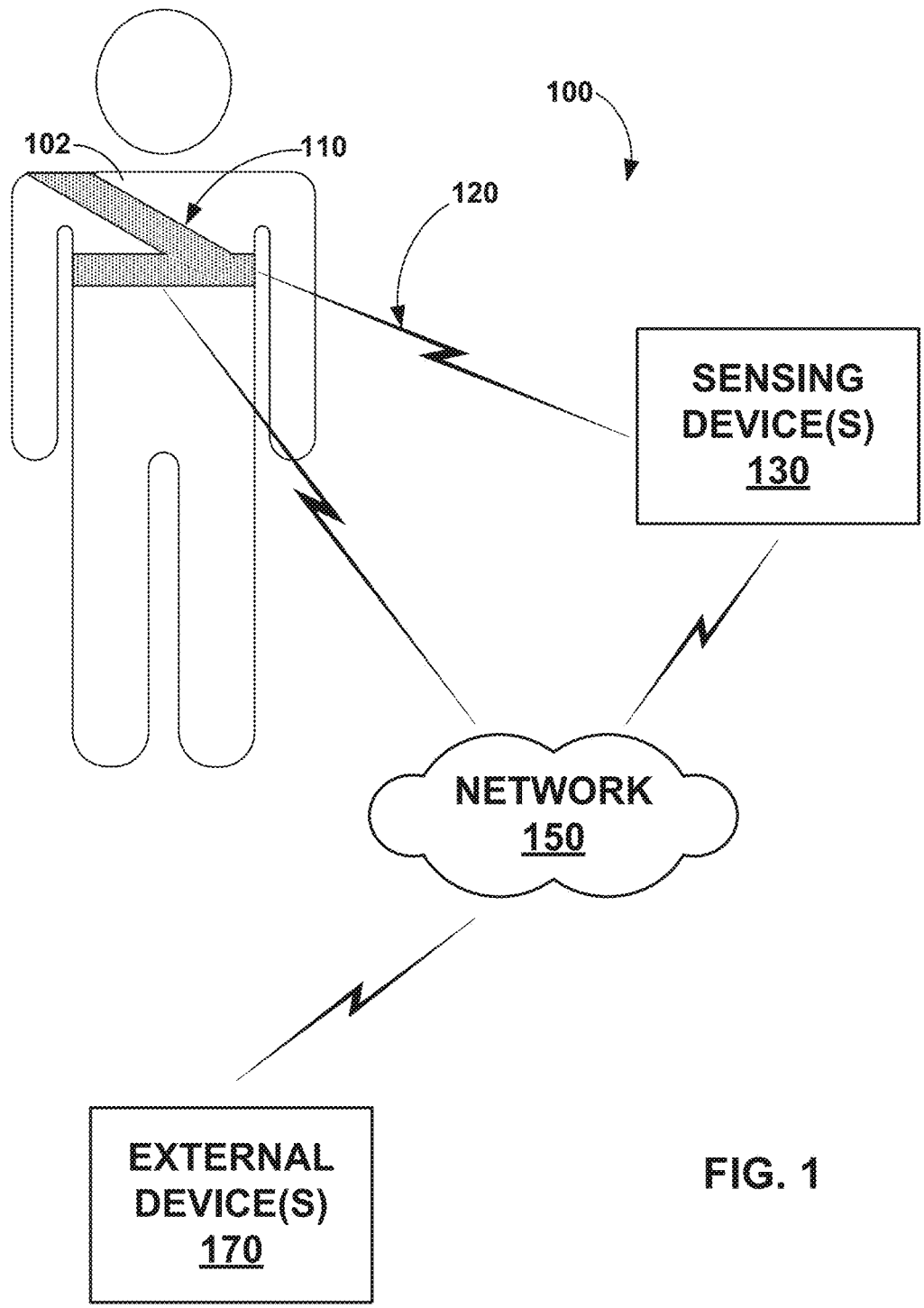
FIG. 1 is a conceptual diagram illustrating an example system configured to apply a machine learning algorithm to data of a patient and provide cardiac defibrillation to the patient according to an example of the techniques of the disclosure.

FIG. 1 is a conceptual diagram illustrating an example system 100 that may be used to deliver therapy to a heart of a patient 102, such as to provide therapy for ventricular fibrillation. System 100 may include an apparatus 110, one or more sensing devices 130, a network 150, and one or more external devices 170. Apparatus 110, in an example, may be worn by patient 102. Apparatus 110 may be a vest apparatus that includes a garment, electronics, and electrodes, as described further herein. Apparatus 110 may be configured to monitor the heart of patient 102, and may configured to provide therapy. In some examples, apparatus 110 includes one or more sense electrodes configured to sense a phenomenon (e.g., a physiological signal such as a cardiac signal) of patient 102. In some examples, apparatus 110 is a WAED.

Sensing device(s) 130 are configured to sense a phenomenon of patient 102 and/or the patient's environment. Apparatus 110 may be configured to sense the same or different phenomena of patient 102 than sensing device(s) 130. As illustrated in FIG. 1, apparatus 110 and sensing device(s) 130 may communicate via one or more links 120. In some examples, links 120 may be Bluetooth® links, such as Bluetooth® Low Energy (BLE) links.

In some examples, apparatus 110 acts as a master for sensing device(s) 130 according to a master/slave relationship. Use of sensing device(s) 130 as slaves for apparatus 110 may improve the overall sensitivity of the machine algorithm implemented by apparatus 110 by, for example, improving true positives while avoiding false positives due to signal interference and false signals. Additionally, communication according to a master/slave relationship may limit the communication-related consumption of a power source of sensing device(s) 130 relative to other, more frequent communication schemes. In such a relationship, apparatus 110 requests data from sensing device(s) 130 only when needed, e.g., when there is a preliminary indication that the patient's state may be not normal based on the cardiac signal (and possibly other data) sensed by apparatus 110.

In some examples, apparatus 110 will wake up a sensing device 130 using a specified magnetic, radio-frequency (RF), or electrical signal. In some examples, once a connection is established between apparatus 110 and sensing device 130, periodic advertisements may maintain the connection. In some examples, organizational or globally unique identifiers may be used by apparatus 110 to distinguish among sensing devices 130. In some examples, communication between apparatus 110 and sensing devices 130 may generally by according to the Bluetooth® or BLE protocols.

Network 150 may represent any single network or combination of networks that facilitate communication between devices. As one example, network 150 may represent a combination of wireless and wired networks (e.g., the Internet) that facilitate communication between one or more external devices 170 and apparatus 110 (and/or sensing devices 130). External devices 170 and network 150 may comprise a remote patient monitoring system, such as the Carelink® network, available from Medtronic plc, of Dublin, Ireland. In some examples, external device(s) 170 comprise one or more servers, and one or more personal computers that a healthcare provider may interact with via a user interface. In some examples, system 100 includes multiple external devices 170 (e.g., a remote patient monitoring system and one or more personal computers). In some examples, external device(s) 170 may comprise a cloud-based computing system.

External device 170 may be configured to receive patient data from apparatus 110 and/or sensing devices 130, and store the data in memory. External device 170 may store data collected from populations of patients. In some examples the population data includes information about patient 102, but in other examples the population data does not necessarily include information about patient 102.

As will be described in greater detail below, apparatus 110 may include a GPU that applies a machine learning algorithm to data for patient 102 to, for example, determine whether fibrillation is detected and whether to deliver defibrillation therapy. Apparatus 110 may deliver defibrillation therapy based on the determination made by the GPU. The data may include data received from sensing device(s) 130. The GPU may update the machine learning algorithm, i.e., the algorithm may learn to better classify future patient data, based on the patient data. External device 170 may also include a GPU and determine updates for the machine learning algorithm based on the patient data, and population data, and provide the updates to defibrillation apparatus 110.

Figure 2:
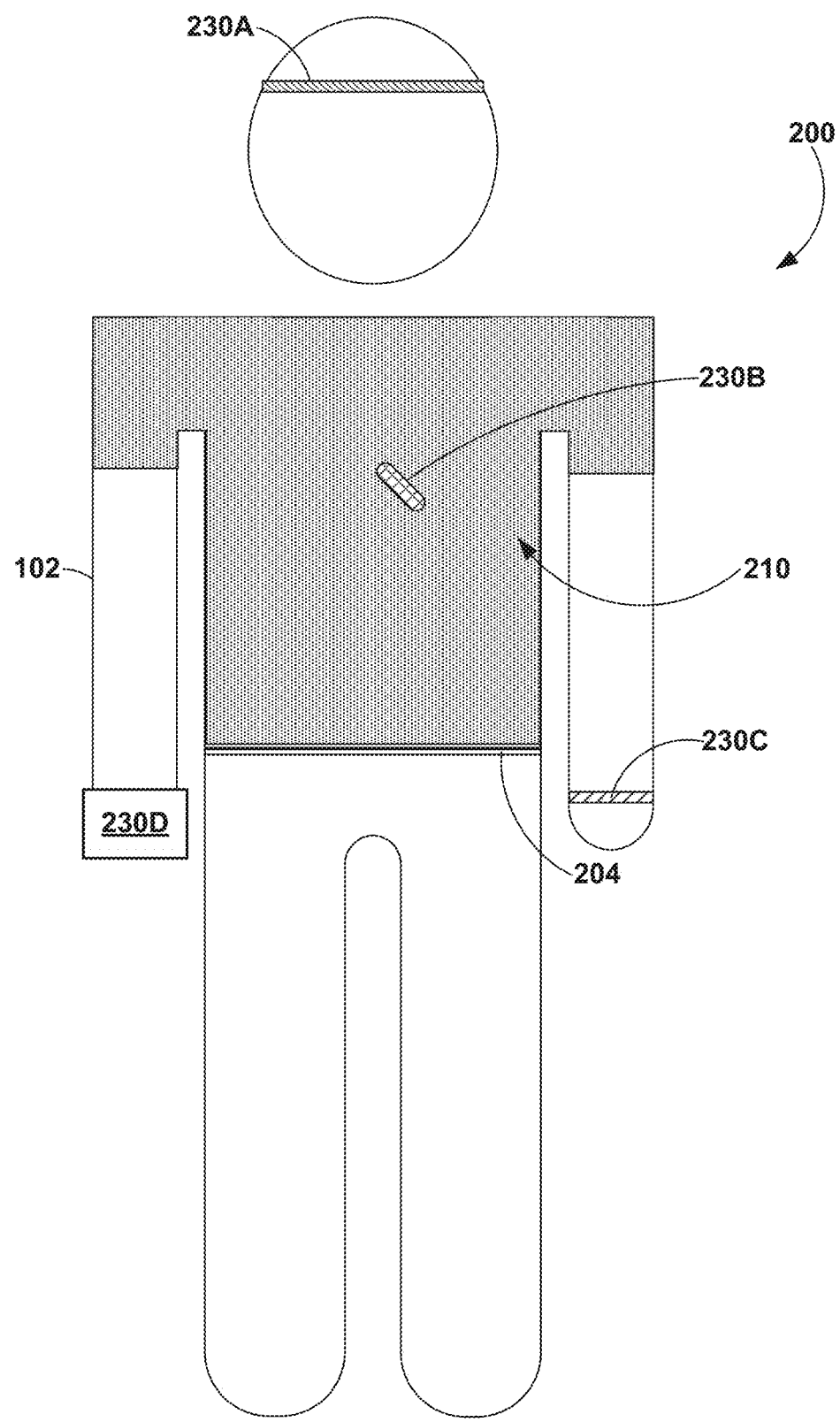
FIG. 2 is a conceptual diagram of another example system configured to apply a machine learning algorithm to data of a patient and provide cardiac defibrillation to the patient according to an example of the techniques of the disclosure.

FIG. 2 is a conceptual diagram of system 200, which is one example of a defibrillation apparatus 110 and sensing devices 130 of system 100 of FIG. 1. System 200 may include apparatus 210, which is one example of apparatus 110. As illustrated, system 200 includes sensing devices 230A-230D (collectively, "sensing devices 230"), although in some examples system 200 may include fewer, more, or different sensing devices 230. In general, patient 102 may be implanted with, wear, or interact with any one or more sensing devices 230. Sensing devices 230 are examples of sensing devices 130 of FIG. 1.

System 200 may include a belt 204. In some examples, belt 204 is part of apparatus 210, and belt 204 is configured to secure portions of apparatus 210 to patient 102 (e.g., a battery pack connected to electronics of apparatus 210). In general, apparatus 210 is configured to be worn by patient 102.

System 200 may be configured for cardiac defibrillation. For example, system 200 includes a variety of sensors (e.g., of apparatus 210 and one or more of sensing devices 230A-230D) configured to sense signals, such as physiological signals of patient 102 and characteristics of the patient's environment. For example, apparatus 210 may include sense electrodes and associated sensing circuitry configured to sense a cardiac signal of patient 102. In some examples, apparatus 210 may be a WAED A sensing device 230, such as sensing device 230B, may include a sensor (e.g., electrodes and associated sensing circuitry) configured to sense a cardiac signal of patient 102. Therefore, the heart of patient 102 may be the source of the signal sensed by apparatus 210 and may also be the source of the signal sensed by sensing device 230B. However, due factors like the location on the body of patient 102 or the type of sensors used, the cardiac signals sensed by different devices may be slightly different (e.g., with respect to type or degree of noise or motion artifact). As such, by including multiple devices, system 200 is configured to determine the state (e.g., normal or not normal) of the heart of patient 102 based on multiple signals. In addition, the use of multiple devices to sense signals coming from the same source (e.g., from the heart of patient 102 or from other part of patient 102) helps to verify a determination of the patient state. In this way, system 200 may have decreased false alarms of non-normal patient states (e.g., a false alarm of a treatable tachyarrhythmia state), which may also be referred to as false positives, relative to systems using only one device. In some examples, false positives due to signal interference and false signals that may be specific to one device or sensing modality may be avoided. Avoiding false alarms may help to avoid delivering unnecessary therapy (e.g., an inappropriate shock). In these and other ways, system 200 may be more reliable over systems that rely only on one device to determine the state of patient 102.

Apparatus 210 may include communication circuitry configured to receive the sensed signals and/or other data derived from the sensed signal from the sensing devices 230. As used herein, the term data may refer to, as examples, signals, data derived from signals, and determinations made based on signals or other data by any device. In some examples, apparatus 210 includes memory configured to store, among other things, the data received from sensing devices 230, the cardiac signal sensed by apparatus 210, and a machine learning algorithm. Apparatus 210 comprises processing circuitry, such as described further herein, which may include a GPU. In some examples, the GPU is configured to apply the machine learning algorithm to the data, e.g., to one or more physiological signals received from sensing devices 230 and the cardiac signal sensed by apparatus 210. The processing circuitry may be configured to determine whether to control the delivery of defibrillation therapy (e.g., via therapy delivery circuitry and defibrillation electrodes of apparatus 210) to patient 102. This determination by the processing circuitry, in some examples, is based on a result of the application of the machine learning algorithm to the physiological signal and the cardiac signal. For example, the processing circuitry may be configured to probabilistically determine one or more states of patient 102 based on the application of the machine learning algorithm to the data, and control delivery of therapy or take one or more other actions based on the determined patient state(s).

An example of a sensing device 230 is sensing device 230A. Sensing device 230A may comprise a headband, hat, or the like configured to be worn on the head of patient 102, and position one or more sensors on the head. Such a sensor may comprise an electroencephalography (EEG) sensor, e.g., electrodes configured to sense and EEG signal and associated sensing circuitry. The sensed EEG signal is one example of the physiological signal described above. For example, apparatus 210 may determine a patient state to, for example, determine whether to deliver defibrillation therapy, based on the EEG signal. Different waveform morphology and timing data of the EEG, as learned from the patient and/or population data, may be associated with either supraventricular or ventricular origin of tachyarrhythmia, and thus useful for the determination of the treatable tachyarrhythmia state, e.g., whether or not the patient state is treatable tachyarrhythmia, of the patient by the machine learning algorithm. The EEG signal data considered by the machine learning algorithm may include data derived from a Lorenz plot or another measure of the amount and/or pattern of variability of the EEG signal. In some examples, apparatus 210 may diagnose specific cardiac conditions, such as atrial fibrillation (AF) via heart rate variability (HRV), based on the ECG and EEG signal data. Apparatus 210 may also determine one or more comorbidity states, such as of epilepsy, or stroke, or other disorders that may be comorbid with cardiac arrhythmia, based on the EEG signal or other data derived from the EEG signal.

Another example of a sensing device 230 is sensing device 230B. Sensing device 230B may be a cardiac monitor (e.g., an implantable cardiac monitor). For example, sensing device 230B may take the form of a Reveal LINQ® Insertable Cardiac Monitor (ICM), available from Medtronic plc, of Dublin, Ireland. As described above, apparatus 210 may sense a first cardiac signal from the heart of patient 102, while patient device 230B senses a second cardiac signal from the heart of patient 102.

Sensing device 230B may also comprise sensors configured to sense other signals indicative of other physiological phenomena of patient 102. For example, sensing device 230B may be configured to sense temperature, posture, activity, blood oxygenation, and tissue perfusion of patient 102. Further, although described herein primarily as a cardiac monitor, sensing device 230B in other examples may be any implantable medical device (IMD) configured to sense one or more physiological signals of patient and, in some examples, to deliver therapy, such as an implantable pacemaker, ICD, neurostimulator, implantable pressure sensor, or drug delivery device. Apparatus 210 may determine a patient state to, for example, determine whether to deliver defibrillation therapy, based on the signals, or other data derived therefrom, sensed by sensing device 230B.

Another example of a sensing device 230 is sensing device 230C. Sensing device 230C may be worn on patient 102, such as on an extremity (e.g., the arm or the wrist). Sensing device 230C is a wearable device, such as a watch or activity monitor comprising one or more sensors, for example. Sensing device 230C may be configured to sense a heart rate, activity, and the concentration of various substances in fluids, e.g., salts in blood or perspiration, of patient 102. Apparatus 210 may determine a patient state to, for example, determine whether to deliver defibrillation therapy, based on the signals, or other data derived therefrom, sensed by sensing device 230C.

Another example of a sensing device 230 is sensing device 230D. Sensing device 230D may be a mobile computing device (e.g., a mobile telephone). As such, sensing device 230D may comprise a microphone, a camera, processing circuitry, and other components that may be used to determine information about or related to patient 102. For example, patient 102 may take a picture of food or drink consumed by patient 102. As another example, sensing device 230D may use GPS or other location techniques to track a location of patient 102. System 200 may automatically track such data and determine the patient state therefrom. For example, system 200 may take into account information regarding the food consumption of patient 102, such as if the patient consumes higher than normal (e.g., higher than a previously determined baseline) amount of a particular type of food (e.g., electrolytes) that may affect the health of patient 102.

Location data collected by sensing device 230D (or another sensing device 230 or apparatus 210) may be used by the systems described herein in a variety of ways. For example, the location data may indicate activities undertaken by the patient and environments or environmental conditions to which the patient is exposed. Apparatus 210 may use this data when determining the state of the patient, e.g., with respect to treatable tachyarrhythmia, respiratory disorders (such as COPD), or other comorbidities that may be particularly influenced by environments to which the patient is exposed. Further, the data collected for a given patient may be marked with location data. In some examples, external devices 170 (FIG. 1) may use location data to demarcate different patient populations for population-based learning by the machine learning algorithm.

Another example of a sensing device 230 is a cardiovascular pressure monitoring device. A cardiovascular pressure monitoring device may be an implantable pressure monitoring device, implantable in a chamber of the heart, the pulmonary artery, or another cardiovascular location, such as the pressure monitoring devices described in commonly-assigned U.S. Pat. No. 8,864,676 to Beasley et al. and U.S. Pat. Pub. No. 2016/0220825 by Greenhut et al., which are incorporated herein by reference in their entirety. In other examples, a cardiovascular pressure monitoring device may be an external pressure monitoring device, e.g., including a cuff-based blood pressure measurement system. The cardiovascular pressure signals produced by such sensors may include values of systolic, diastolic, or mean pressures, including pulmonary artery pressure or peripheral vascular pressure, as examples. The pressure signals, e.g., morphology or trends of the signal, may indicate a present or predicted treatable tachyarrhythmia state, or comorbidities, such as heart failure and COPD.

In some examples, one or more sensing devices 230 may provide signals or values for pulse rate, oxygen saturation, and respiration rate. In some examples, sensing device comprises an integrated pulse oximetry system providing values or signals for these parameters. The trends or morphology of these parameters may indicate a present or predicted treatable tachyarrhythmia state, or comorbidities, such as heart failure and COPD.

Although primarily described herein as implanted or worn, sensing devices may be any device configured to collect data about the patient or the patient's environment. Another example of a sensing device 230 may be a glucose monitor configured to sense a physiological signal of patient 102 (e.g., a glucose concentration). Other examples of sensing devices 230 include a spirometer, a medical imaging device, a food scale, or an air quality sensing device.

In general, such as described further herein, signals sensed by one or more sensing devices, or other data derived from such signals may be used by machine learning algorithms to determine the state of patient 102. For example, apparatus 210 may determine a tachyarrhythmia state of the patient, e.g., whether or not the patient is experiencing or will likely experience a treatable tachyarrhythmia, and whether to deliver defibrillation, or another therapy configured to terminate or prevent tachyarrhythmia, based on the determined state. Apparatus 210 may be configured to deliver therapy based on the determinations. In some examples, apparatus 210 may be configured to additionally determine whether a comorbidity, such as COPD, has manifested in patient 102 based on application of the machine learning algorithm to such data.

Figure 3:
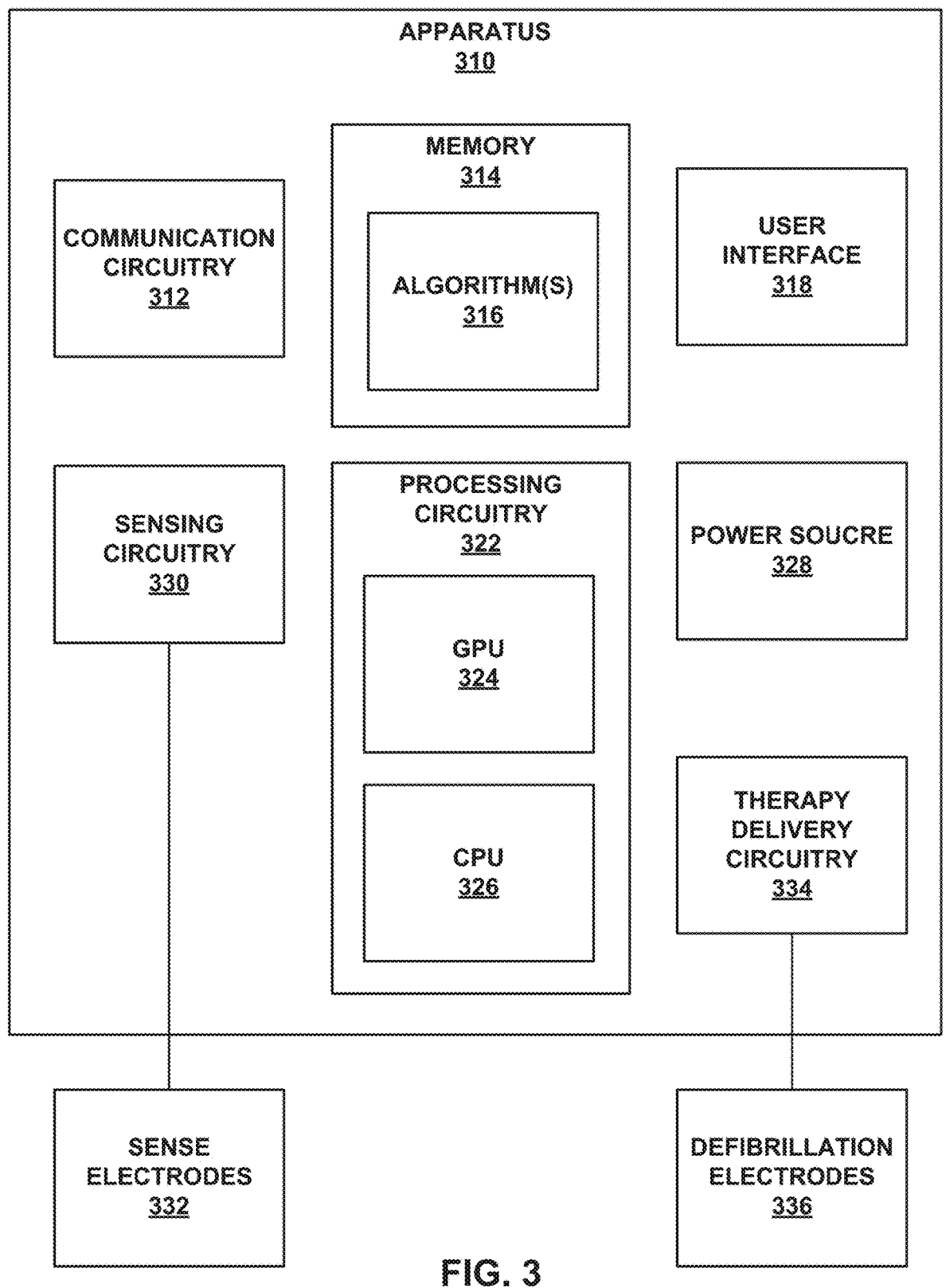
FIG. 3 is a block diagram of an example configuration of a defibrillation apparatus that may implement a machine learning algorithm and provide cardiac defibrillation to the patient according to an example of the techniques of the disclosure.

FIG. 3 is a block diagram of an example configuration of a defibrillation apparatus 310, which may be an example of apparatus 110 of FIG. 1 or apparatus 210 of FIG. 2. Apparatus 310 may comprise communication circuitry 312, a memory 314, a user interface 318, processing circuitry 322, a power source 328, sensing circuitry 330, sensing electrodes 332, therapy delivery circuitry 334 and defibrillation electrodes 336. Sensing circuitry 330 is electrically coupled to sense electrodes 332, and therapy delivery circuitry 334 is electrically coupled to defibrillation electrodes 336. Processing circuitry 322 may comprise a GPU 324 and a CPU 326. Memory 313 may be configured to store one or more algorithms 316.

Communication circuitry 312 includes any suitable hardware, firmware, software, or any combination thereof for communicating with another device (e.g., any device described herein, such as sensing devices 130 of FIG. 1 or external devices 170 of FIG. 1). Communication circuitry 312 may be configured to transmit or receive radiofrequency ("RF") signals via an antenna (not shown), or other signals via a wired connection with another device or a network. Communication circuitry 312 may be configured for such communication with other devices, such as sensing devices 130 or 230, or external devices 170. As examples, communication circuitry may include resistors, inductors, capacitors, amplifiers, and/or transistors configured generate, modulate, filter, and/or demodulate signals according to any of a variety of communication protocols. In some examples, communication circuitry 312 may be coupled to one or more electrodes, and configured with similar circuitry to transmit and receive signals via the electrodes for tissue conductance communication (TCC).

In general, any device described herein may be configured to communicate with any other device (e.g., any device described herein may comprise communication circuitry like that of communication circuitry 312). In some examples, communication circuitry 312 may be configured to communicate via Bluetooth® (e.g., transmit or receive Bluetooth® RF signals). For example, communication circuitry 312 may be configured to transmit or receive a BLE radio signal. In some cases, communication circuitry 312 comprises a BLE module. In some examples, multiple elements of system 100 are connected to one another via Bluetooth® connection.

In some examples, communication circuitry 312 comprises input circuitry configured to receive a signal from another device. In some examples, communication circuitry 312 comprises output circuitry configured to transmit information from apparatus 310 to another device. For instance, communication circuitry 312 may comprise circuitry configured to transmit information about a patient state to external device 170.

Communication circuitry 312 may send information to another device or to a network (e.g., network 150 of FIG. 1) on a continuous basis, at periodic intervals, or upon request from another device. Communication circuitry 312 may also send a command to another device for sending information to apparatus 310. For example, communication circuitry 312 may be configured to send a command to a sensing device 130 or 230 to command the sensing device to transmit a physiological or other signal, or data derived from such a signal, to apparatus 310.

Memory 314 may store instructions that cause processing circuitry 322 to provide the functionality described herein, and information used by processing circuitry 322 to provide the functionality ascribed to apparatus 310 as described herein. Memory 314 may include any volatile, non-volatile, magnetic, optical, or electrical media, such as a random-access memory (RAM), read only memory (ROM), non-volatile RAM (NVRAM), electrically-erasable programmable ROM (EEPROM), flash memory, or any other digital or analog media. Memory 314 may also include a removable memory portion that may be used to provide memory updates or increases in memory capacities. A removable memory may also allow patient data to be easily transferred to another computing device, or to be removed before apparatus 310 is used to for another purpose (e.g., upgrade, clean, or resize the garment of apparatus 310).

Memory 314 may be configured to store one or more algorithms 316. For example, algorithm 316 may comprise a machine learning algorithm. The machine learning algorithm may be configured to determine one or more states of patient 102. In an example, the machine learning algorithm is applied via processing circuitry 322, e.g., GPU 324, to data about patient 102, such as physiological signals or data derived from the signals. The machine learning algorithm may be automatically updated, e.g., continue to learn, based on new data stored in memory 314, via processing circuitry 322. In the case of signals, the data may comprise amplitude and temporal information (e.g., an electrocardiogram (ECG) with a measured voltage over time). In general, the data may include values that vary over time, and the machine learning algorithm may consider features of such a signal, or changes in such features over time.

Memory 314 may be configured to store data about patient 102 or the patient's environment. In some examples, such data is sensed by a sensing device 130 or 230. For example, memory 314 may be configured to store data about the environment that the patient was in at a particular time, e.g., as indicated by location data, fluid state information (e.g., hydration level or edema), and patient health record information. Memory 314 may be configured to store data about patient 102 in tables, lists, or graphical formats.

User interface 318 may be configured or otherwise operable to receive input from a user, such as patient 102 or a healthcare provider. User interface 318 may be configured to display information to the user. For example, user interface 318 may comprise one or more lights, a display, a motor configured to provide a vibration alert (e.g., similar to "vibrate" mode on a smartphone), a speaker configured to alert the user of an indication. Patient 102 may interact with user interface 318, which may include display configured to present graphical user interface to the patient, and a keypad or another mechanism for receiving input from the patient.

In some examples, patient 102 or a caregiver interacts with user interface 318 to provide information to system 100. For example, patient 102 or the caregiver may contribute to the development of the machine learning algorithm by providing feedback about an event. For example, user interface 318 may indicate to patient 102 that therapy is indicated based on the state of patient 102, but patient 102 may override the delivery of therapy (e.g., if patient 102 knows that therapy should not be indicated or that the detection is a "false positive"). For example, user interface 318 comprises one or more buttons (e.g., digital or physical buttons). Although illustrated in the example of FIG. 3 as being part of apparatus 310, the user interface through which a patient or another user may provide feedback, also referred to as reinforcement, for reinforced learning by the machine learning algorithm, may be a user interface provided by any one or more computing devices. For example, the user interface may be a user interface of a smart telephone, wearable device (e.g., smart watch), or a dedicated device for communicating with apparatus 310.

The patient or caregiver provides information about the false alarm via the user interface, and the machine learning algorithm may be adjusted based on the new information about the false alarm. The reinforcement from the user may be in near real-time, e.g., as soon as the patient or caregiver reacts to the determination by the machine learning algorithm. Adjustments to the machine learning algorithm may include adjusting weights and/or connections between nodes, as examples.

Processing circuitry 322 may be configured to carry out the techniques described herein. Processing circuitry 322 may include fixed function processing circuitry or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 322 herein may be embodied as firmware, hardware, software or any combination thereof. Processing circuitry 322 may control other elements in system 100 of FIG. 1. In some examples processing circuitry 322 may control other devices (e.g., patient devices 130 or 230).

In some examples, processing circuitry 322 includes GPU 324. In general GPU 324 may be configured to apply the machine learning algorithm to the data collected by apparatus 310, e.g., via sensing circuitry 330 and/or from sensing devices 130 or 230, which may include patient signals (e.g., one or more physiological signals from sensing devices and the cardiac signal sensed by sensing circuitry 330). GPU 324 may be configured to automatically update the machine learning algorithm, such as based on the collected information, updates determined by external device 170 based on population data, determinations made by other devices, such as a sensing device 130 or 230, or patient or other user inputs. GPU 324 may comprise a plurality of parallel cores, which enable parallel application of data sets including variety of different data from various sources to the machine learning algorithm.

With reference to FIG. 1, external device 170 may also comprise a GPU. In an example, GPU 324 of apparatus 310 may comprise a first GPU. The GPU of the external device may comprise a second GPU. Any processing circuitry described herein, including the first and second GPUs, may be configured to perform the techniques attributed to processing circuitry 322 or the processing circuitry of the external device, in some examples.

Based on learning from sets of data, e.g., regarding patient 102, the machine learning algorithm may discover patterns in, and relationships, between several independent and interdependent variables derivable from the data. Ongoing consideration of these variables, or other learned variables from continued updating of the algorithm, may allow the machine learning algorithm to probabilistically determine, e.g., classify, diagnose, and/or predict, a state of the patient. The machine learning algorithm may be configured to employ any one or more of Bayesian, random forest, decision tree, linear regression, deep learning, neural network and/or dimensionality reduction techniques, as examples. In some examples, a result of the application of the machine learning algorithm to the data, e.g., one or more physiological signals from sensing devices 130 or 230 and/or the cardiac signal from sensing circuitry 330 includes classification of the data, e.g., the cardiac signal and physiological signal (individually or collectively) as one of normal or not normal, or indicating one or more other states of the patient, such as whether a treatable tachyarrhythmia is indicated or predicted, or whether one or more comorbidities are indicated or predicted.

In some examples, processing circuitry includes CPU 326. In general, CPU 326 may be configured to control the activities of the components of apparatus 310, such as communication circuitry 312, user interface 318, sensing circuitry 330, and therapy delivery circuitry 324. CPU 326 may also be configured to acquire data for consideration by GPU 324, and control the functionality of GPU 324. In some examples, CPU 326 is configured to execute an arrhythmia detection algorithm (e.g., a treatable tachyarrhythmia detection algorithm). The arrhythmia detection algorithm may be stored in memory 314. In some examples, CPU 326 is configured to update the tachyarrhythmia detection algorithm based on a result of the application of the machine learning algorithm to the data (e.g., a physiological signal sensed by a patient device and the cardiac signal sensed by the apparatus). CPU 326, for example, is configured to control the delivery of defibrillation therapy (e.g., whether or not defibrillation is delivered) based on the result of the application of the machine learning algorithm to the physiological signal the cardiac signal. In some examples, CPU 326 may be configured to control delivery of other therapies by therapy delivery circuitry 334 based on the result of the application of the machine learning algorithm to the physiological signal and the cardiac signal, such as therapies configured to prevent a predicted arrhythmia.

Power source 328 delivers operating power to various components of apparatus 310. Power source 328 may include a small rechargeable or non-rechargeable battery and a power generation circuit to produce the operating power. Recharging may be accomplished through a wired connection to a voltage source, or through proximal inductive interaction between an external charger and an inductive charging coil within apparatus 310. Power source 328 may comprise replaceable batteries, in some examples, and apparatus 310 may be configured such that patient 102 may access the cavity where power source 328 is stored to replace the batteries.

In some examples, sensing circuitry 330 may be configured to generate a signal. In some examples, sensing circuitry 330 comprises amplifiers, filters, analog-to-digital converters, and other circuitry configured to generate and condition signals for receipt by processing circuitry 322. Sensing circuitry 330 may be coupled to sense electrodes 332, and may, for example, receive cardiac electrical signals from various combinations of two or more sense electrodes 332. Sensing circuitry 330 may be configured to sense cardiac events attendant to depolarization and repolarization of cardiac tissue.

Sensing circuitry 330 may include one or more sensing channels, each of which may be selectively coupled to respective combinations of sense electrodes 332 to detect electrical activity of the heart. Different sense electrodes 332 may be positioned within apparatus 310 in a position to effectively measure cardiac signals of patient 102. Each sensing channel may be configured to amplify, filter and rectify the cardiac electrical signal received from selected electrodes coupled to the respective sensing channel to detect cardiac events, such as R-waves, and may also include an analog-to-digital converter to provide a digitized representation of the time-varying signal to processing circuitry 322. Processing circuitry 322, e.g., GPU 326, may determine, from the sensed cardiac signal, whether the cardiac signals indicate a normal or not normal state and, if not normal, whether the cardiac signals indicate one of a plurality of not normal sub-classifications, such as bradycardia, treatable tachyarrhythmia, syncope, noise from the signal (e.g., 60 Hertz noise), motion artifacts, or loss of signal. In some examples, apparatus 310 may include sensors for sensing any of a variety of physiological or other signals described herein in addition to sensing the cardiac signal.

The data set applied to the machine learning algorithm may include a variety of data from a variety of sources that include values that change over time. In the case of signals, the data may comprise amplitude and temporal information, e.g., an electrocardiogram (ECG) with a measured voltage over time. In general, the machine learning algorithm may consider features of a signal formed by changing values over time, or changes in such features over time. For example, in the case of a cardiac signal, the variables may relate to features of the cardiac signal, such as the P-wave, R-wave, QRS-complex, S-T segment, Q-T interval, and T-wave, as well as heart rate and heart rate variability. The variables may be related to the morphology of the signal, such as slope, area under curve, or maximum or minimum amplitude or width of morphological features of the signal. Other variables related to morphology of the signal may include values or features identified by a Fourier or wavelet transform, a turning point algorithm, or other signal transform or decomposition techniques. The variables may include differences over time and/or relative to baselines of such features, rates of change of such features, or differences in such features between different sensing vectors. Signals having features that may be evaluated by the machine learning algorithm in this manner are not limited to a physiological signal, but may instead be values of any measurable or derivable parameter over time, such as R-R interval length or variability, or other parameters derivable from an ECG, that may form a trend-based curve.

Therapy delivery circuitry 334 may be coupled to defibrillation electrodes 336. In some examples, therapy delivery circuitry 334 is configured to deliver a therapy shock to the heart of patient 102, such as based on a determination that patient 102 has a non-normal cardiac state, such as an occurring or predicted treatable tachyarrhythmia. For example, if patient 102 has fibrillation or other treatable tachyarrhythmia, apparatus 310 may deliver therapy to patient 102 via defibrillation electrodes 336. In some examples, therapy delivery circuitry 334 may be configured to deliver various types of therapy (e.g., pacing and/or defibrillation, or in some instances, drug therapy). In some examples, the therapy is preventative, such as pacing or drug therapy configured to a treatable tachyarrhythmia predicted by the machine learning algorithm. In examples in which the therapy comprises electrical pulses, e.g., pacing or defibrillation, therapy delivery circuitry 334 may include one or more capacitors, charge pumps, current sources, or other signal generation circuitry, as well as switching circuitry to couple the signal to electrodes 336. In examples in which the therapy comprises a drug therapy, therapy delivery circuitry 334 may comprises circuitry configured to generate a signal to drive a pump.

Figure 4:
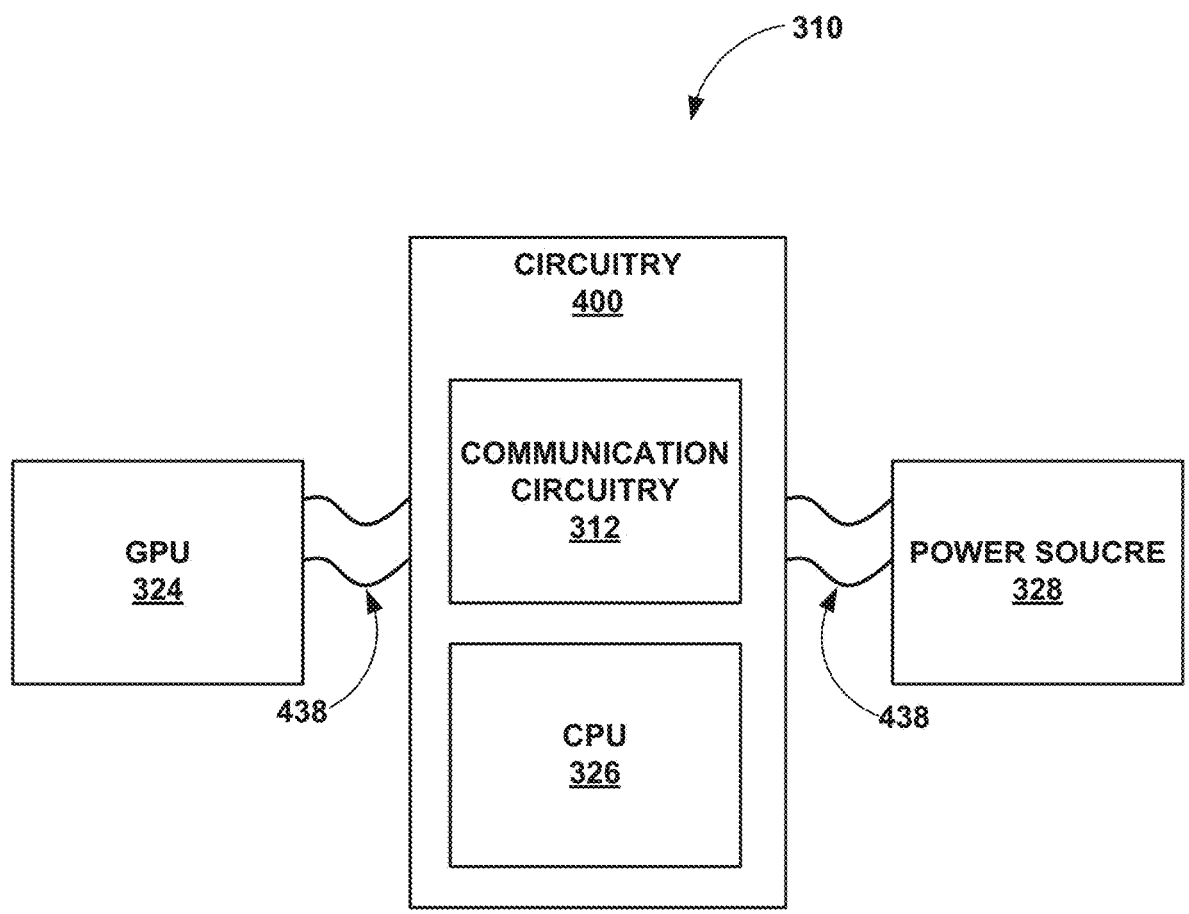
FIG. 4 is a block diagram of an example configuration of certain components of the defibrillation apparatus of FIG. 3.

FIG. 4 is a block diagram illustrating an example configuration of certain components of apparatus 310. As illustrated by FIG. 4, apparatus 310 may comprise various elements connected to one another by a flex material 438. In particular, GPU 324 is connected to circuitry 400, and circuitry 400 is connected to power source 328, by flex material 438. Circuitry 400 may comprise communication circuitry 312 and CPU 326, and in some examples sensing circuitry 330 and therapy delivery circuitry 334 (not shown in FIG. 4). In general, the separation of the relatively larger GPU 326 and power source 328 from the other components of apparatus 310, and the flex material connections, may provide a particular form factor for apparatus 310, e.g., that may be more easily worn by patient 102.

Flex material 438 may provide electrical connections between the components of apparatus, e.g., may include conductors running through, on, or between layers of flexible material. In some examples flex material 438 comprises a rigid flex electronic substrate construction. Such a construction may enable various form factors for apparatus 410, such as a body band (e.g., wearable band with embedded electronics that may include a shoulder strap), or a headband that has sensors integrated therein.

Figure 5:
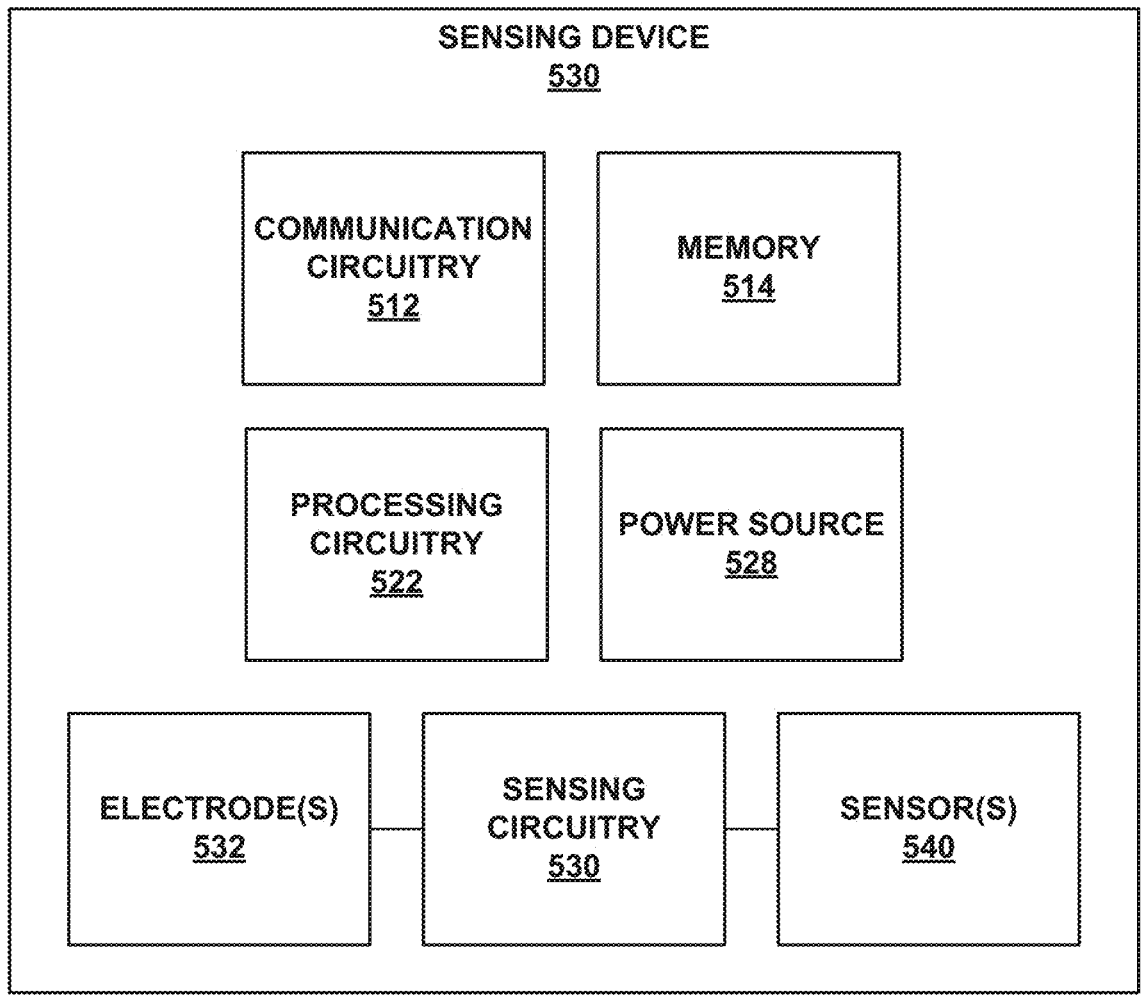
FIG. 5 is a block diagram of an example configuration of a sensing device that may sense a physiological phenomenon of the patient according to an example of the techniques of the disclosure.

FIG. 5 is a block diagram of an example configuration of a sensing device 530, which may be an example of sensing devices 130 of FIG. 1 and/or sensing devices 230 of FIG. 2. In the illustrated example, and similar as described with respect to sensing device 230B of FIG. 2, sensing device 530 may take the form of a Reveal LINQ® Insertable Cardiac Monitor (ICM), available from Medtronic plc, of Dublin, Ireland. In other examples, patient device 530 may take the form of any of the sensing devices described herein, such as those described with respect to FIG. 2, or other types of sensing devices.

Figure 6:
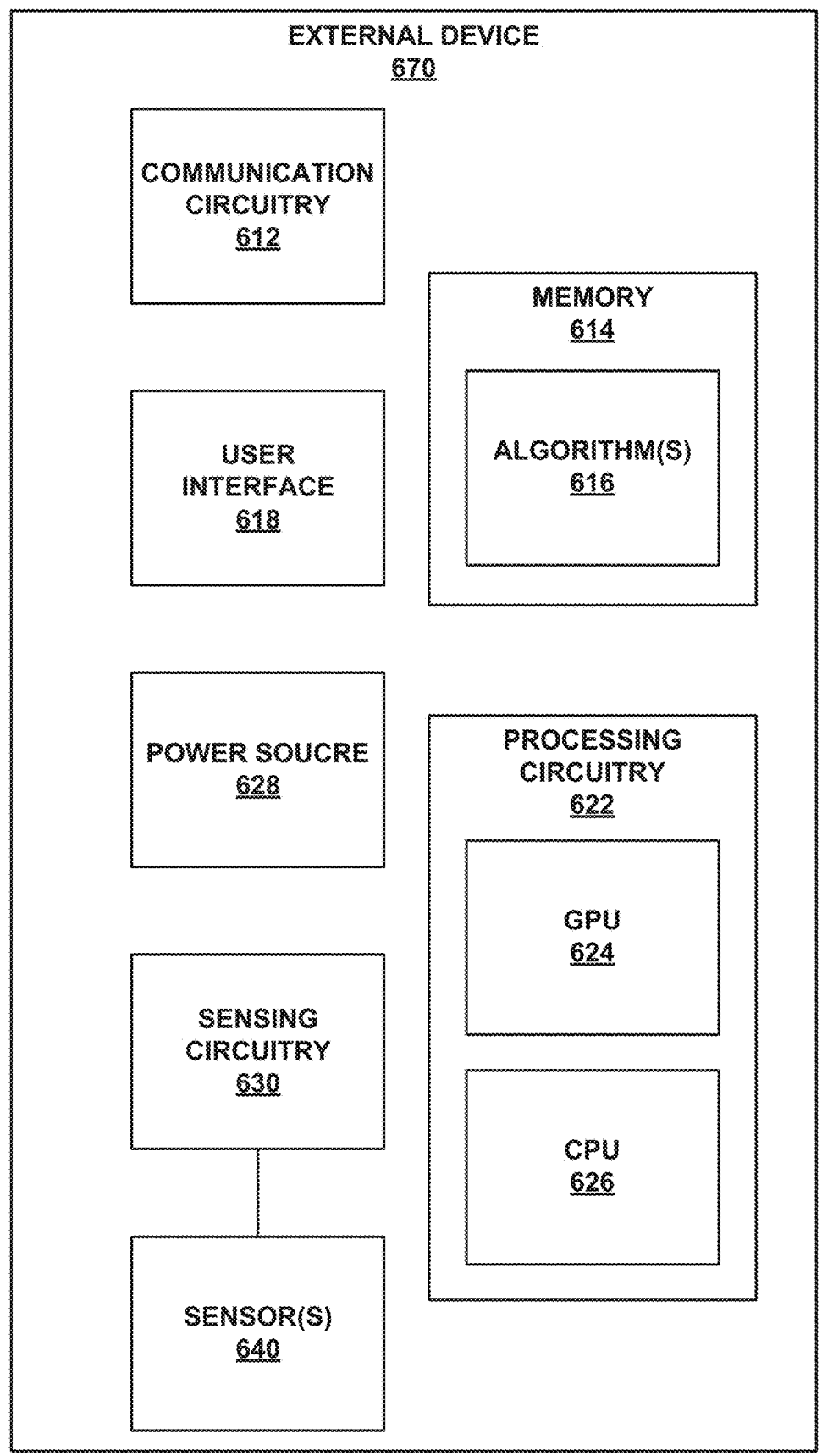
FIG. 6 is a block diagram of an example configuration of an external device configured to receive data from defibrillation apparatuses and update machine learning algorithms according to an example of the techniques of the disclosure.

FIG. 6 is a block diagram of external device 670, which may be an example of external device 170 of FIG. 1. With reference to both FIGS. 5 and 6, the following elements may have at least the same configuration and function as similar elements as described with respect to FIG. 3. For example, communication circuitry 512 and communication circuitry 612 may have the same or similar functionality as communication circuitry 312. For example, memory 515 and memory 614 may have the same or similar functionality as memory 314. Although one or more algorithms 616 are illustrated as stored within memory 614, memory 614 may be configured to store other information, such as any information described herein. Similarly, memory 514 may be configured to store any information described herein.

Processing circuitry 522 and processing circuitry 622 may have the same or similar functionality as processing circuitry 322. Processing circuitry 622 is illustrated as including GPU 624, which may have the same or similar functionality as GPU 324 (except as noted herein, in some examples), and CPU 626, which may have the same or similar functionality as CPU 326. Power source 528 and power source 628 may have the same or similar functionality as power source 328. User interface 618 may have the same or similar functionality as user interface 318, or any other interface described herein.

Sensing circuitry 530 and sensing circuitry 630 may have the same or similar functionality as sensing circuitry 330. One or more sensors 540 and one or more sensors 640 may take the form of sensors described, for example, with respect to patient devices 230 of the example of FIG. 2. In some examples, such a sensor may comprise an accelerometer, an optical sensor, a pressure sensor, an air or blood flow sensor, a temperature sensor, or an air quality sensor. One or more electrodes 532 may have the same or similar functionality as sense electrodes 332, e.g., sensing circuitry 530 may be configured to sense a physiological signal of patient 102, such as a cardiac signal, via the electrodes. In some examples, the cardiac signal comprises information, such as about an R-R interval, an amplitude of an R-wave, a QRS width, or an R-R interval variability. In an example, inputs to the machine learning algorithm include such data from the cardiac signal.

In some examples, external device 670 and/or sensing device 530 may be configured to detect information about the environment of patient 102. For example, external device 670 and sensing device 530 may be configured to determine an air temperature and/or quality in the environment patient 102 is in.

In some examples, memory 514 of sensing device is configured to store, and processing circuitry 522 execute, a tachyarrhythmia detection algorithm. The processing circuitry 522 may store in memory 514 indications of whether tachyarrhythmia was detected at various times. Processing circuitry 522 of sensing device 530 may provide such indications to apparatus 310 via communication circuitry 512. As described herein, GPU 324 of apparatus 310 may use these indications of the determination of tachyarrhythmia by sensing device 530 as inputs for the machine learning algorithm, for assistance in classifying a current patient state, and/or as feedback for adaptation of the machine learning algorithm.

Rather than continuous or periodic communication, apparatus 310 and sensing device 530 may communicate as master and slave, respectively, in a master/slave relationship. Communication according to a master/slave relationship may limit the communication-related consumption of power source 528 of sensing device 530 relative to other, more frequent communication schemes. In such a relationship, apparatus 310 requests data from sensing device 530 for use by machine learning algorithm only when needed, e.g., when there is a preliminary indication that the patient's state may be not normal based on the cardiac signal (and possibly other data) sensed by apparatus 310.

Algorithms 616 stored in memory 614 of external device 670 (as illustrated in FIG. 6) may comprise one or more machine learning algorithms, and GPU 624 may be configured to implement the machine learning algorithms. In some examples, GPU 624 is more computationally capable then GPU 324 of apparatus 310. The greater computational capability may be due to a variety of factors, such as number of cores or clock speed. Size of processing circuitry, controlling power consumption, and heat may be of lesser concern in the case of external device 670 then apparatus 310, particularly where apparatus 310 is wearable by patient 102.

GPU 624 may be configured to implement a relatively more computationally intense version of the machine learning algorithm than GPU 324, which may implement a "lite" version of the machine learning algorithm. In some examples, GPU 624 updates the machine learning algorithm differently than GPU 324. For example, GPU 624 may update the machine learning algorithm based on population data and, in doing so, update the machine learning algorithm based on a significantly greater number of data sets than GPU 324. CPU 626 may control communication circuitry 612 to send the determined updates to apparatus 310, and GPU 326 may update its instance of the machine learning algorithm as indicated by external device 670.

The machine learning algorithm implemented by GPU 324 of apparatus 310 may be updated in a variety of ways. For example, GPU 324 may automatically update the machine learning algorithm based on the data it receives and considers. In some cases, the learning may be reinforced by feedback, such as from a user or an independent determination from another device, e.g., sensing device 530. Additionally, GPU 324 may update the machine learning algorithm as indicated by the updates determined by GPU 624 when considering population data. In this manner, the machine learning algorithm implemented by GPU 324 is updated based on population data. In some examples, the population-based updates to the machine learning algorithm may include new weights on variables applied to normal variance factors for different populations. In general, the updates may also include updates to the graph structure of the algorithm, or updates to the parameters/variables considered by the algorithm, the latter of which may be more intense and determined by GPU 624.

CPU 626 may receive, via communication circuitry 612 data sets from a number of different apparatuses 310 of a number of different patients 102. CPU 626 may also receive or otherwise determine information indicate into which patient population(s) the received data should be sorted. GPU 624 may implement a number of population-specific machine learning algorithms, and apply the data for a given population to the algorithm for the population in order to determine updates for the machine learning algorithms of apparatuses 310 of patients in those populations.

Different populations may have different characteristics. For example, each population may be defined by a unique combination of values for a plurality of characteristics that distinguish the populations. Example characteristics include age, gender, location, body mass index (BMI), weight, blood pressure (e.g., ranges such as low, ideal, pre-high or borderline high, and high), respiration, glucose level, history of adverse medical events, and presence of other comorbid medical conditions.

The normal and/or not normal ranges for various parameters or variables that are inputs to the machine learning algorithm may vary between different patient populations. For example, the resting heart rate for bradycardia is expected to increase with age, and the resting normal heart rate is expected increase with BMI and blood pressure. Adapting the machine learning algorithm based on data sets of patients with characteristics similar to each other may increase the ability of the algorithm to correctly characterize the state of a given patient within the population.

Figure 7:
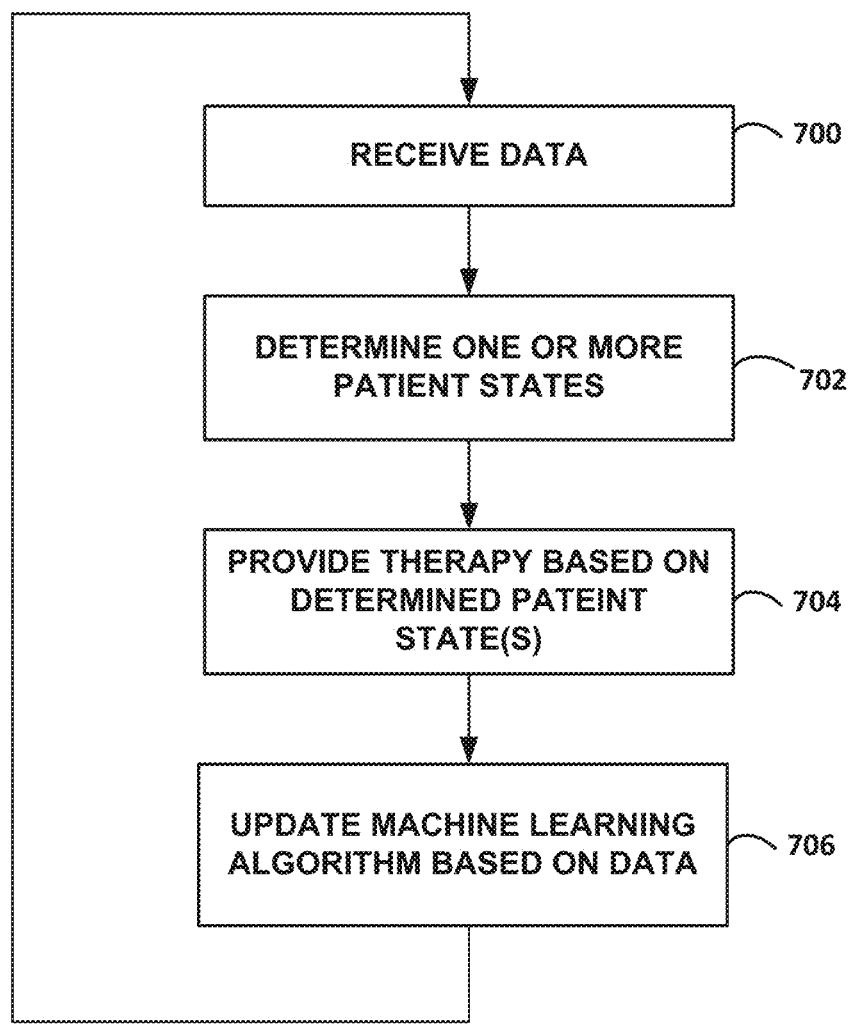
FIG. 7 is a flowchart illustrating an example technique that may be implemented by a defibrillation apparatus to apply a machine learning algorithm to data and determine whether to deliver therapy.

FIG. 7 is a flowchart illustrating an example technique that may be implemented by a defibrillation apparatus 310 to apply a machine learning algorithm to data and determine whether to deliver therapy. For example, apparatus 310 receives data (700). The data includes a cardiac signal sensed by apparatus 310. The data may also include data from sensing devices, such as another cardiac or other physiological signal, or data derived therefrom.

Apparatus 310 applies a machine learning algorithm to the data to characterize the data, and thus one or more states of the patient, as normal or not normal (702). In some examples, the machine learning algorithm may indicate whether a treatable tachyarrhythmia state is not normal, e.g., indicating the presence of fibrillation or another shockable tachyarrhythmia. In some examples, the machine learning algorithm may additionally or alternatively indicate whether the state for one or more other conditions, e.g., comorbidities, of the patient is normal or not normal, such as whether an episode or worsening of COPD or another comorbidity is present or predicted. Apparatus 310 decides whether or not to provide a therapy and, in some cases, which of a plurality of therapies to apply, based on the characterization, e.g., in response to certain not normal characterizations (704). The therapy may be defibrillation shock. If the characterization is predicted treatable tachyarrhythmia, the therapy may be cardiac pacing or another therapy configured to prevent a predicted tachyarrhythmia.

Apparatus 310 also updates the machine learning algorithm based on the considered data (706). For example, a GPU 324 may update the machine learning algorithm autonomously and/or based on feedback from a user or another device, e.g., sensing device 230. As described herein, GPU 324 may also update the machine learning algorithm based on population data, e.g., according to population-based updates received from external device 670. Population-based updates may occur less frequently than autonomous and reinforced updates.

Figure 8:
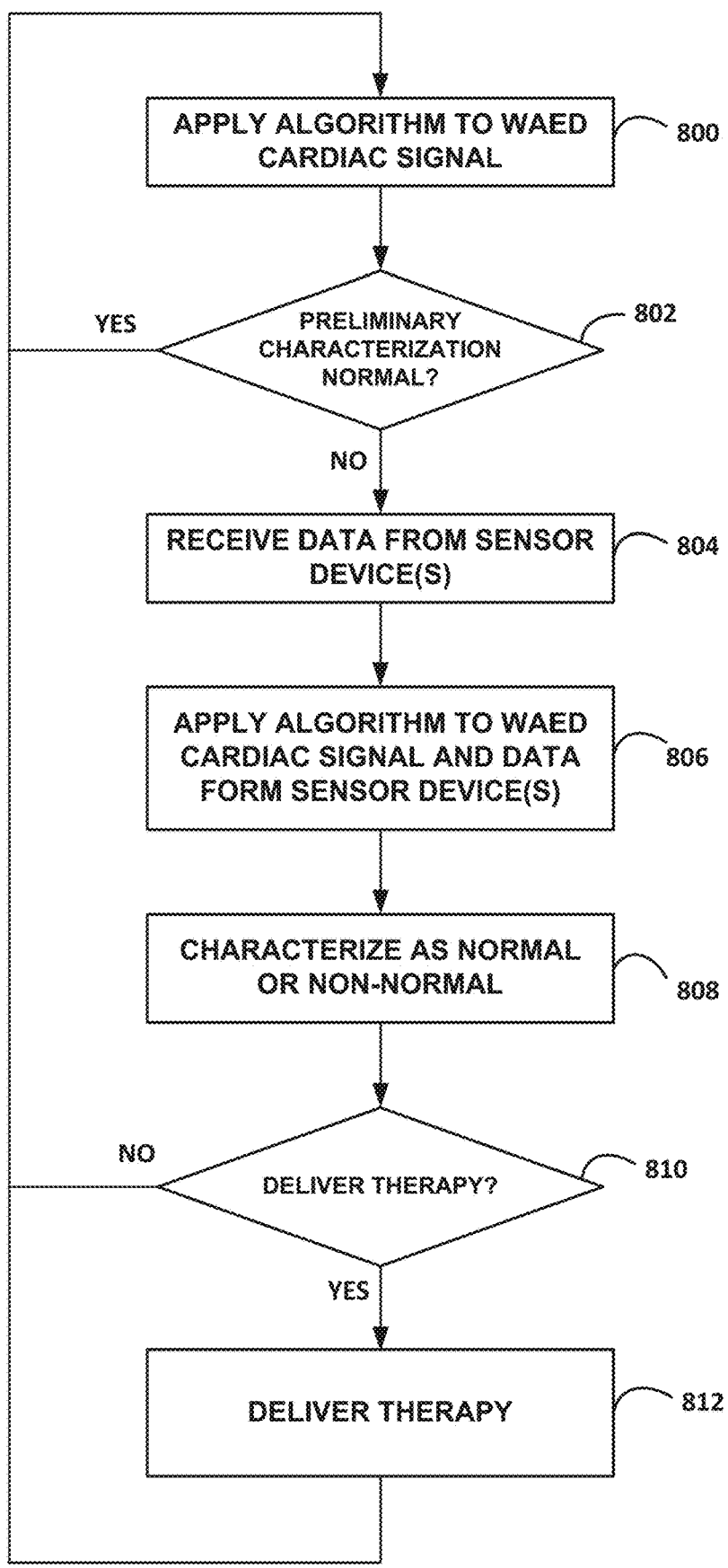
FIG. 8 is a flowchart illustrating an example technique that may be implemented by a defibrillation apparatus to apply a machine learning algorithm to data including data received from one or more sensing devices and determine whether to deliver therapy.

FIG. 8 is a flowchart illustrating an example technique that may be implemented by a defibrillation apparatus 310 (referred to as the WAED in the figure) to apply a machine learning algorithm to data, including data received from one or more sensing devices 530, and determine whether to deliver therapy. According to the example of FIG. 8, GPU 324 applies the machine learning algorithm to the cardiac signal sensed by sensing circuitry 330 via electrodes 332 (800). Based on the application of the machine learning algorithm to the cardiac signal, GPU 324 determines whether a preliminary characterization of the patient state is normal (802). If the preliminary characterization is normal (YES of 802), GPU 324 continues to apply the algorithm to a new data set derived from the cardiac signal sensed by apparatus 310 (800).

If the preliminary characterization is not normal (NO of 802), CPU 326 receives data from one or more sensing devices 530 via communication circuitry 312 (804). For example, apparatus 310, acting as a master in a master/slave relationship, may initiate a communication session with one or more sensing devices 530 to command the sensing devices to provide the data. The data may include a cardiac signal or other physiological or environmental signal sensed by the sensing device, data derived therefrom, and/or determinations made by the sensing device based on the signals/data.

GPU 324 applies the machine learning algorithm to the cardiac signal and the data from sensing device(s) 530 (806). Based on this application of the algorithm, GPU 324 characterizes the state, e.g., the treatable tachyarrhythmia state as normal or not normal (808). CPU 326 determines whether to provide a therapy to patient 102 based on the characterization (810). If CPU 326 determines that therapy should be delivered (YES of 810), CPU 326 may control therapy delivery circuitry 334 to deliver therapy, e.g., pacing or defibrillation via electrodes 336 (812). In some examples, CPU 326 may take other actions based on the characterization, such as changing a sensing vector, or setting of an adjustable filter or amplifier to ameliorate a source of noise based on characterization of the signal as noisy. Although not illustrated in FIG. 8, GPU 324 may update the machine learning algorithm, e.g., based on the characterization of the data and, in some cases, feedback received from users or other devices regarding the characterization of the data, such as whether the patient canceled the delivery of therapy.

Although the examples of FIGS. 7 and 8 include delivery of therapy, e.g., a defibrillation shock, in response to a not normal characterization, therapy is not necessarily delivered in all examples according to the techniques of this disclosure. In some examples, the machine learning algorithm makes determinations of the state of the patient without apparatus responsively delivering therapy. Such determinations may be recorded in memory of the apparatus, transmitted to an external device via a network, and/or presented to a user via a user interface. Determinations of patient state without therapy delivery may occur, for example, during a reinforced learning phase of the machine learning algorithm.

Figure 9:
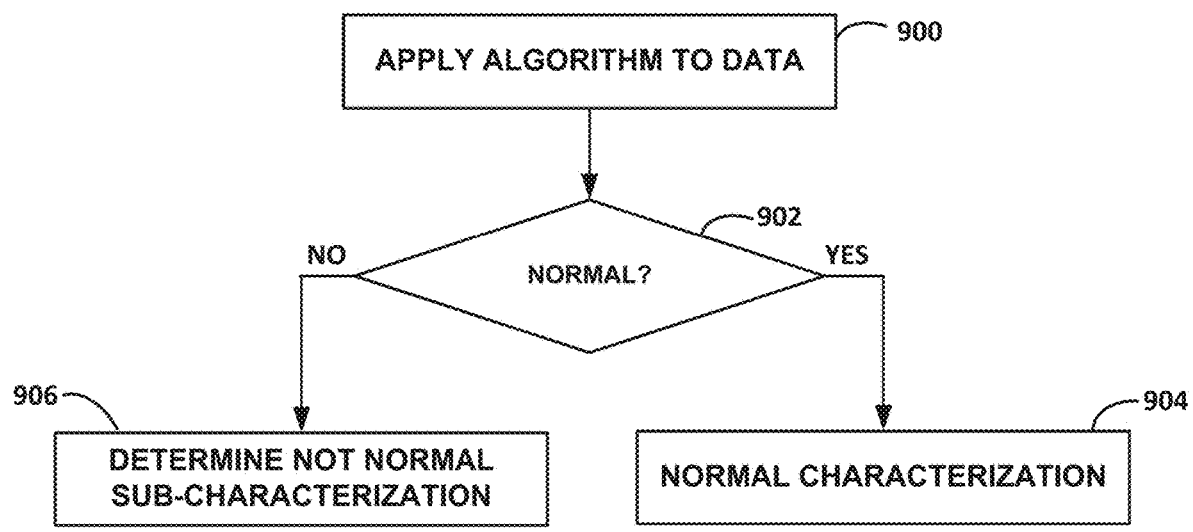
FIG. 9 is a flowchart illustrating an example technique that may be implemented by a defibrillation apparatus to apply a machine learning algorithm to data to characterize a patient state as normal or not normal.

FIG. 9 is a flowchart illustrating an example technique that may be implemented by a defibrillation apparatus 310 to apply a machine learning algorithm to data to characterize a patient state as normal or not normal. According to the example of FIG. 9, GPU 324 applies the machine learning algorithm to data (900), and determines whether the data indicates a normal state (902). The machine learning algorithm may employ Bayesian, random forest, decision tree, linear regression, deep learning, neural network and/or dimensionality reduction techniques, as examples. In some examples, the machine learning algorithm employs a Bayes network with different weights for different factors (e.g., variables) derivable from the ECG and other data. In some examples, the spectrums of values represented by heat maps, such as those described with respect to FIGS. 15-32, may be used to relate the weights to some output. If the data indicates a normal state (YES of 902), GPU 324 returns a normal characterization, e.g., to CPU 326 (904). In some examples, the machine learning algorithm is probabilistic, and configured to indicate a not normal state if the probability of the normal state is below a certain percentage, such as 95%, 99%, 99.9%, or any range between any of these values. These values are examples, and other, e.g., lower, percentages may be used in some examples. Sensitivity and specificity of the machine learning algorithm may increase over time as the algorithm learns based on how many learning cycles and the size of the population from which data for learning is derived. In some examples, the probability may initially have a first value, such as 95%, but increase to another value, such as 99.9% or more, over time.

Example variables that may be derived from ECG data and considered by the machine learning algorithm include R-wave amplitude, R-R interval length, R-R interval variability, QRS width, or the slope, area under curve, or other morphological features of a signal formed from values of R-wave amplitude, R-R interval length, R-R interval variability, or QRS width over time. In some examples, a rolling window (e.g., of three minutes or some other length) of values of each variable is considered. In some examples, a window of normal training set data for a variable will have values that satisfy a boundary condition at least a threshold amount (e.g., percentage) of time during the window, such as 99%. Examples of normal and not normal data sets and associated boundary conditions for different variables are discussed below with respect to FIGS. 15-32.

In some examples, if the characterization is not normal (NO of 902), the algorithm considers the data (and in some cases additional data) to determine a not normal sub-characterization (906). The algorithm structure for determining the not normal sub-characterization may be a fault decision tree. Possible not normal sub-characterizations include bradycardia, treatable tachyarrhythmia, non-treatable tachyarrhythmia (e.g., atrial fibrillation or another supra-ventricular tachyarrhythmia), syncope, 60 Hertz noise, motion artifacts, loss of signal, electrode peeling, or high R-R interval variability, e.g., due to atrial fibrillation.

Figure 10:
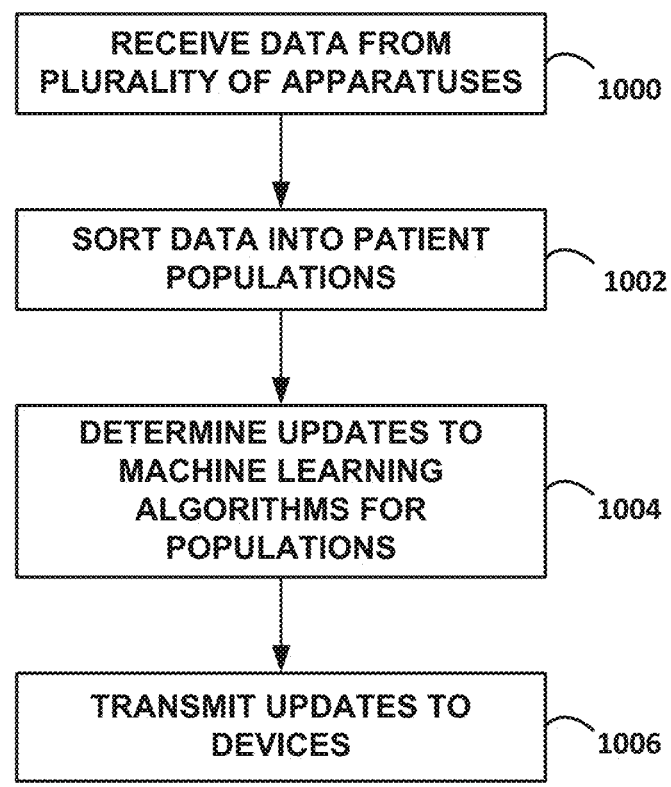
FIG. 10 is a flowchart illustrating an example technique that may be implemented by an external device to determine updates for machine learning algorithms for different populations based on population data.

FIG. 10 is a flowchart illustrating an example technique that may be implemented by an external device 670 to determine updates for machine learning algorithms for different populations based on population data. According to the example of FIG. 10, external device 670 receives data from a plurality of different apparatuses of a plurality of different patients (1000). External device 670, e.g., CPU 626, sorts that data into a plurality of different patient populations (1002). As described herein, different patient populations may be distinguished from each other based on one or more of age, gender, location, obesity classification, weight or body mass index (BMI), blood pressure, respiration, glucose level, medical history, presence of other comorbid medical conditions, such as COPD or diabetes, type and/or model of defibrillation apparatus, and type(s) and/or model(s) of sensing devices available. Based on the sorted data, GPU 624 determines updates for different machine learning algorithms for the different patient populations (1004). As described herein, updates to the machine learning algorithm may include new weights on variables, updates to the graph structure of the algorithm, or updates to the parameters/variables considered by the algorithm, as examples. External device 670, e.g., CPU 626 and communication circuitry 612, communicate the updates for each population to the various apparatuses in that population (1006). The updates may be provided to the defibrillation apparatus via any wired or wireless connection, e.g., via the Internet, and in some cases via one of the sensing (slave) devices acting as an intermediary.

Figure 11:
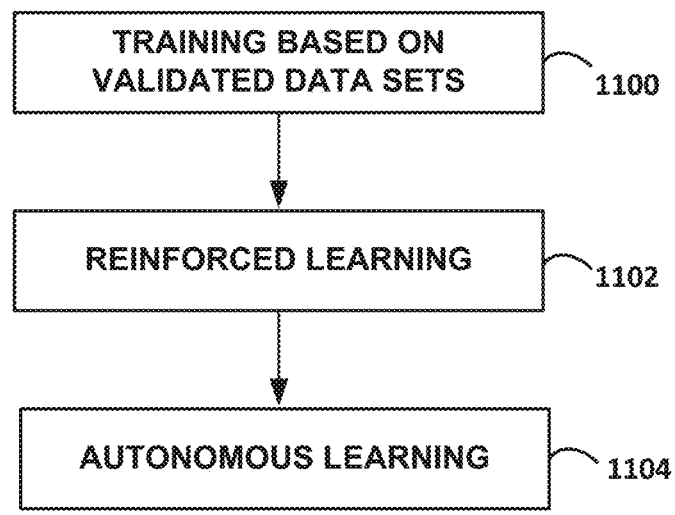
FIG. 11 is a flowchart illustrating different learning phases of a machine learning algorithm.

FIG. 11 is a flowchart illustrating different learning phases of a machine learning algorithm. Initially, the machine learning algorithm may be designed and trained, e.g., using one or more external devices 670. The initial training may include application of numerous validated data sets to the algorithm, e.g., data sets validated by a domain expert as having a particular classification (1100). In some examples, the validated data sets are data sets from a population having particular characteristics, and the machine learning algorithm is intended for use in an apparatus for patient within that population.

When apparatus 310 is in use by patient, the machine learning algorithm may undergo a period of reinforced learning (1102). During reinforced learning, apparatus 310 may receive feedback from a user via user interface 318 and/or from another device (e.g., sensing device 530) regarding whether the determination of state by the machine learning algorithm was correct. In some examples, new data (including new patterns in, and relationships, between variables) available from the patient (or a population of similar patients) may reviewed and classified by one or more physicians for additional reinforced learning by the machine learning algorithm. After some time, e.g., after reinforced learning has achieved a desired level of sensitivity and specificity in the algorithm, manual intervention may no longer be required. The machine learning algorithm may continue autonomous learning (1104).

Figure 12:
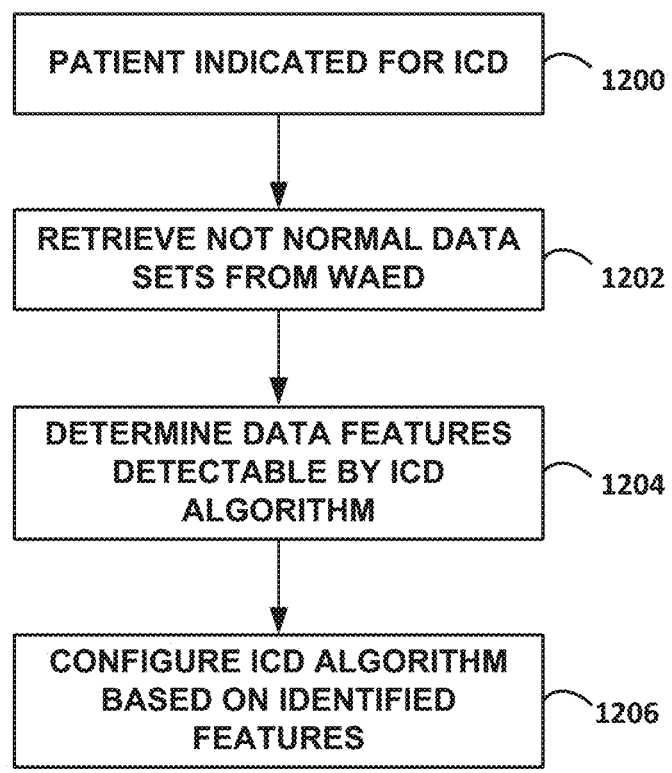
FIG. 12 is a flowchart illustrating an example technique for configuring a tachyarrhythmia detection algorithm of an implantable cardioverter defibrillator for a patient based on data previously evaluated by a machine learning algorithm of a defibrillation apparatus of the patient.

FIG. 12 is a flowchart illustrating an example technique for configuring a tachyarrhythmia detection algorithm of an implantable cardioverter defibrillator (ICD) for a patient based on data previously evaluated by a machine learning algorithm of a defibrillation apparatus 310 of the patient. The example technique of FIG. 12 may be performed by external device 670 and/or one or more other computing devices.

According to the example of FIG. 12, patient 102 is indicated for implantation of an ICD, at which time patient 102 will likely stop using apparatus 310 (1200). External device 670 retrieves data sets characterized as not normal and, in some cases, tachyarrhythmia, by the machine learning algorithm of apparatus 310 of patient 102 (1202). External device 670 processes the data sets to identify features in the data that are detectable by the tachyarrhythmia detection algorithm of the ICD (1204). The tachyarrhythmia algorithm of the ICD may not include a GPU or machine learning algorithm, and may be not be able to detect tachyarrhythmia in the same manner as apparatus 310. As an example of identification of features the data sets detectable by the ICD, external device 670 may partition an ECG waveform (or sequence or signal of variable values derived from the ECG waveform) of a certain length from a data set classified by apparatus 310 into a plurality of shorter sequential waveforms or smaller sequential sets of values of a variable. External device 670 may identify features in the sequential waveforms or value sets that the ICD may detect in sequence (rather than in parallel as may have been done by GPU 324) to detect a tachyarrhythmia. External device 670 configures the ICD tachyarrhythmia detection algorithm based on the identified features (1206).

Figure 13:
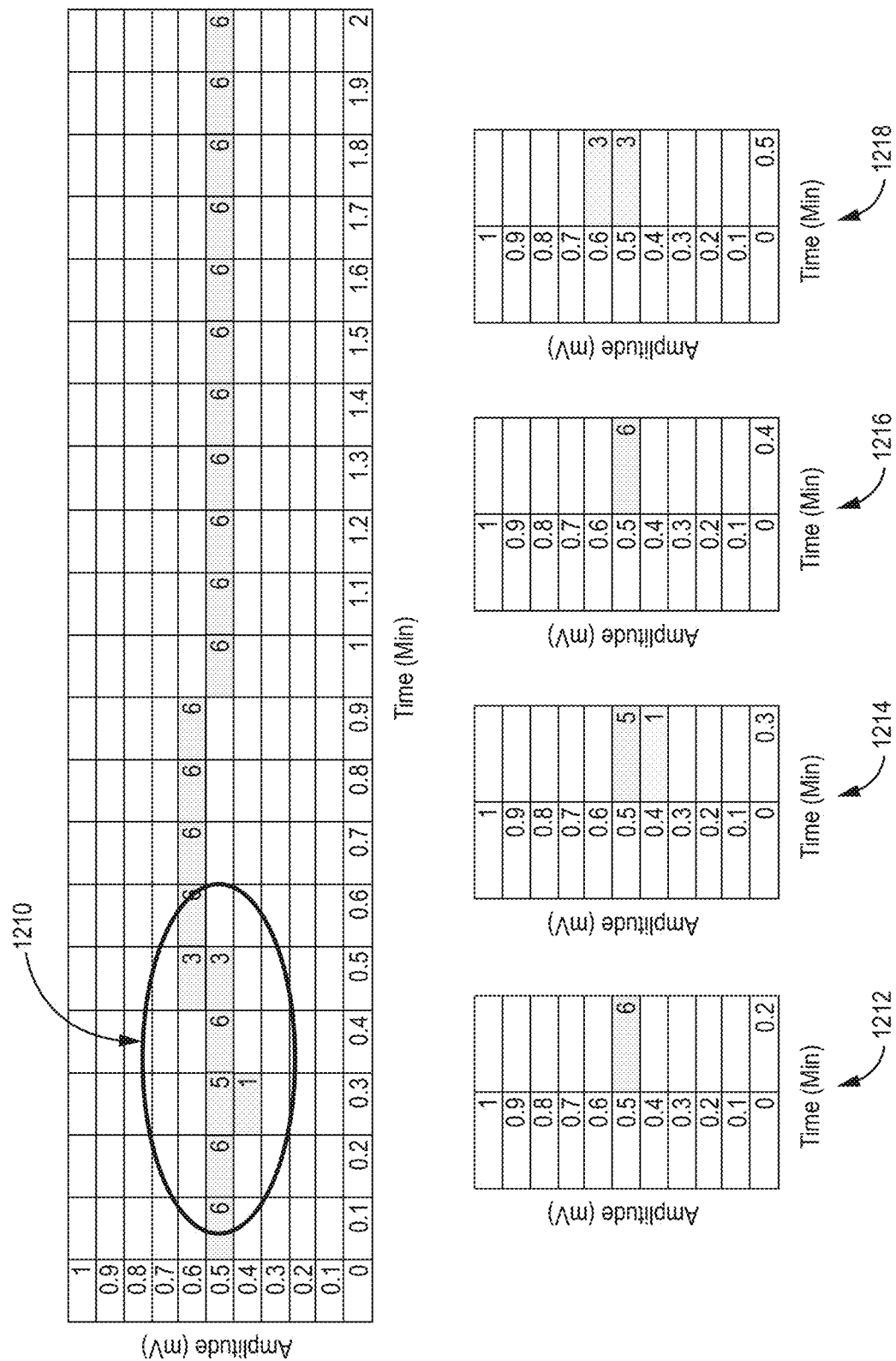
FIG. 13 is a diagram illustrating an example technique for parsing data evaluated by a machine learning algorithm to configure a tachyarrhythmia detection algorithm of an implantable cardioverter defibrillator.

FIG. 13 is a diagram illustrating an example technique for parsing data evaluated by a machine learning algorithm to configure a tachyarrhythmia detection algorithm of an implantable cardioverter defibrillator. In particular, FIG. 13 illustrates a heat map of two minutes of consecutive R-wave amplitude values. In the heat map, the R-wave amplitude values are binned within the 0.1 minute interval in which the R-wave occurred, and within one of ten 0.1 mV amplitude ranges between 0 and 1 mV. In this example heat map, each 0.1 minute interval included six R-waves and, accordingly, six R-wave amplitude values.

The R-wave amplitude values in the heat map of FIG. 13 may represent a set of consecutive R-wave amplitude values that would be characterized by a machine learning algorithm as not normal—particularly the sequence of R-wave amplitude values in region 1210 of the heat map where the amplitudes were more variable. Although data considered by a machine learning algorithm is presented herein the in the form of heat maps, consideration of data by a machine learning algorithm according to the techniques described herein does not necessarily involve conversion of the data into a heat map format. Rather, data is presented in heat map format for ease of illustration of certain features of the data.

As illustrated by FIG. 13, processing circuitry, e.g., processing circuitry 622 of external device 670, may parse the consecutive amplitude values represented by region 1210 into shorter segments represented by bins 1212-1218. The processing circuitry may further determine a feature of the data identifiable by the ICD based on the parsed data segments. For example, based on the data represented by bins 1212-1218, the processing circuitry may determine a threshold level of R-wave amplitude variability above which a not normal state, e.g., a treatable tachyarrhythmia state, is indicated or predicted. The threshold level of variability determined from the segments represented by bins 1212-1218 may, as examples, be a threshold amount of variability over a particular period of time, a threshold amount of variability in each of N consecutive time periods, and/or a threshold amount of variability in M of N consecutive time periods. The threshold level of variability may be programmed into the ICD for the particular patient and used by the ICD, e.g., with other tachyarrhythmia detection or discrimination techniques, to identify treatable tachyarrhythmia.

Processing circuitry, e.g., processing circuitry 322 of apparatus 310, may use an inverse of the parsing technique illustrated by FIG. 13 to merge together shorter segments of data, e.g., from sensing devices 230, into a larger data set, e.g., a trend-based curve for application to the machine learning algorithm. In some examples, the length of a segment of consecutive data values stored by sensing devices 230 and transmitted to apparatus 310 may be limited, e.g., due to memory, communication, or other capabilities of the sensing devices 230. When apparatus 310 receives data from sensing devices 310, e.g., as requested according to the master-slave relationship, the shorter segments may be time-stamped, and the processing circuitry may combine the shorter segments in order to form a larger data set for application to the machine learning algorithm. In some examples, any known data padding techniques may be applied to the data received from sensing device 230 to produce a data set having sufficient values for consideration by the machine learning algorithm.

Figure 14:
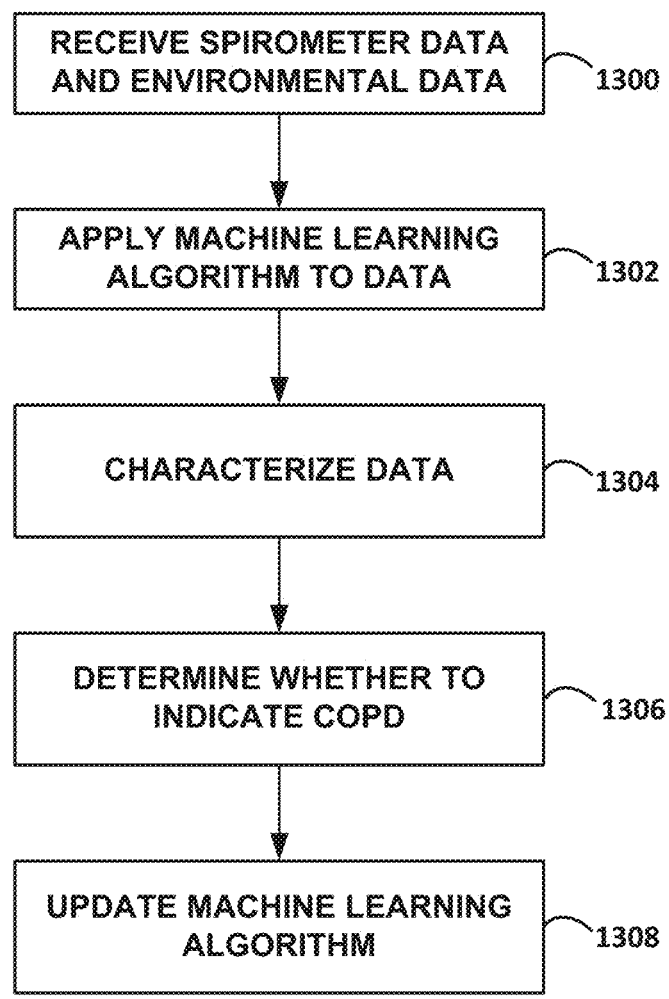
FIG. 14 is a flowchart illustrating an example technique for applying a machine learning algorithm of a defibrillation apparatus to data to determine whether to provide an indication of chronic obstructive pulmonary disease.

FIG. 14 is a flowchart illustrating an example technique for applying a machine learning algorithm of a defibrillation apparatus 310 to data to determine whether to provide an indication of chronic obstructive pulmonary disease. Although apparatus 310 may primarily function to detect and treat tachyarrhythmia, GPU 324, the ability to collect diverse data from sensing devices 530, and the ability to adapt the machine learning algorithm based on population data collected by external device 670 may make apparatus 310 a platform to additionally or alternatively determine whether patient 120 is experiencing a variety of comorbid conditions or disorders. One example comorbidity that may be evaluated by apparatus 310 is COPD.

According to the example of FIG. 14, apparatus 310 receives spirometer data and environmental data from one or more sensing devices 530, e.g., a spirometer and an environmental sensor (1300). GPU 324 applies the machine learning algorithm (or distinct portion thereof for evaluating COPD) to the data (1302). Example data that may be evaluated for COPD is described below with respect to FIGS. 28-30. The machine learning algorithm characterizes the data (1304). In some examples, GPU 324 compares each of the spirometer and environmental data to one or more thresholds, and determines a COPD state of the patient using a decision tree based on whether a threshold, or particular combinations of thresholds for different data, are met. CPU 326 determines whether to provide an indication of COPD for patient 102, e.g., via user interface 318 or to external device 670 via a network, based on the characterization (1306). GPU 324 updates the machine learning algorithm based on the data and the characterization (1308).

Figure 15:
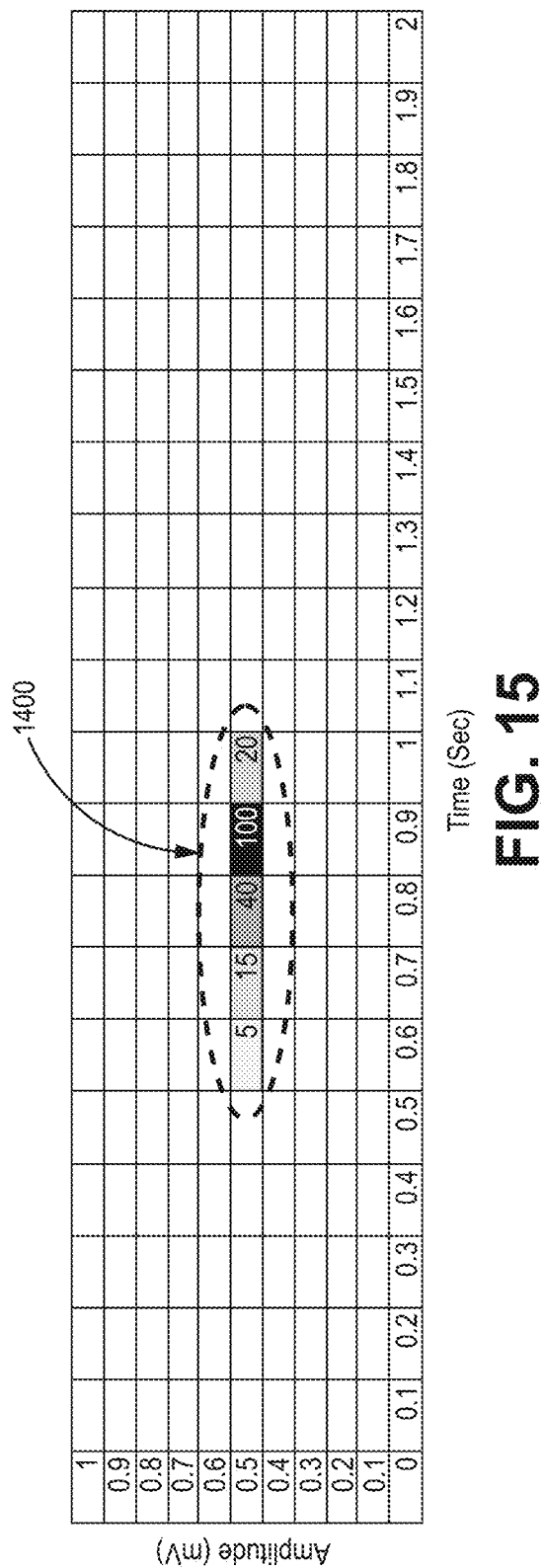
FIG. 15 is a diagram illustrating data from a cardiac signal that a machine learning algorithm would learn to classify as normal according to an example of the techniques of this disclosure.

FIG. 15 is a diagram illustrating data from a cardiac signal that a machine learning algorithm would learn to classify as normal, e.g., the treatable tachyarrhythmia state is normal or not treatable tachyarrhythmia, according to an example of the techniques of this disclosure. More particularly, FIG. 15 is a heat map plot of occurrences of combinations of R-R interval and R-wave amplitude in a normal data set, with each beat binned within one of the 0.1 mV amplitude bins between 0 and 1 mV and one of the 0.1 second R-R interval length bins between 0 and 2 seconds. Region 1400 illustrates the distribution of such values in a normal data set. In particular, region 1400 includes consistent R-wave amplitudes within a 0.1 mV range including 0.5 mV, and beats distributed as shown in within the 0.1 second R-R interval length bins between 0.5 and 1 seconds, with the greatest number of beats having R-R interval lengths between about 0.7 and 0.9 seconds. R-wave amplitude, R-R interval, R-wave amplitude as a function of R-R interval, and a distribution or variability of R-wave amplitude as a function of R-R interval are examples of variables that may be considered by a machine learning algorithm to characterize data for a patient.

Figure 16:
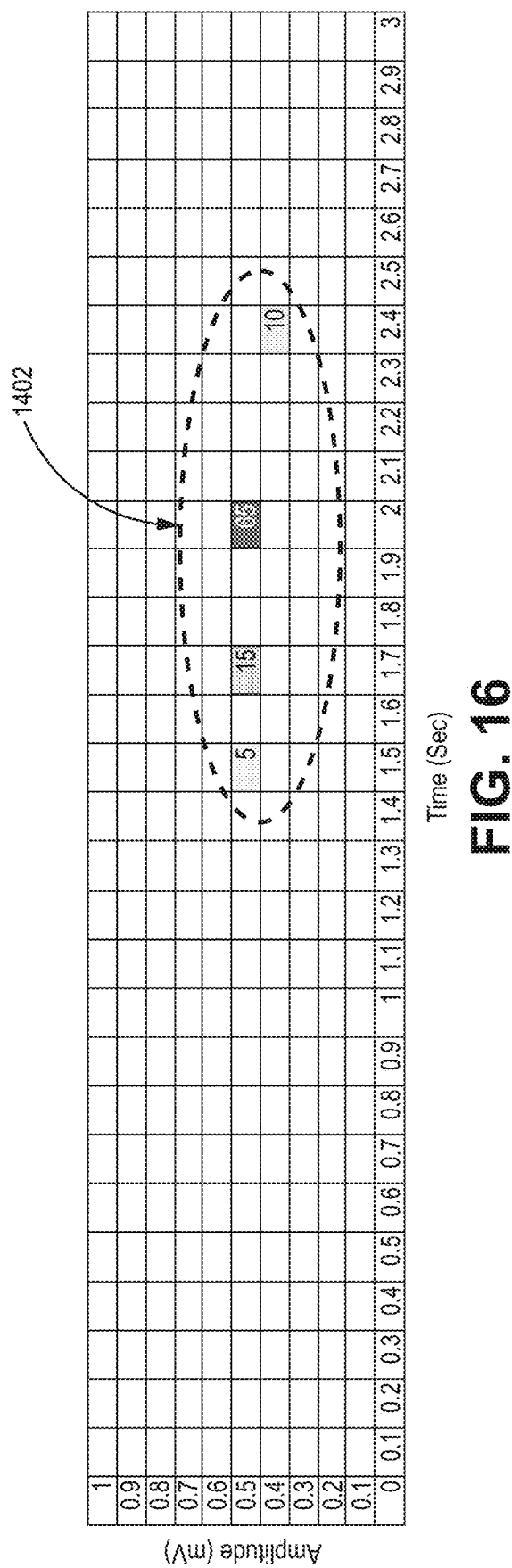
FIGS. 16-22 are diagrams illustrating data from a cardiac signal that a machine learning algorithm would learn to classify as not normal according to examples of the techniques of this disclosure.

FIGS. 16-22 are diagrams illustrating data from cardiac signals that a machine learning algorithm would learn to classify as not normal according to examples of the techniques of this disclosure. For example, FIG. 16 is a heat map plot of occurrences of combinations of R-R interval and R-wave amplitude in a not normal data set and, more particularly, a data set that would be classified as bradycardia, with each beat binned within one of the 0.1 mV amplitude bins between 0 and 1 mV and one of the 0.1 second R-R interval length bins between 0 and 3 seconds. Region 1402 illustrates the distribution of such values in bradycardia set. In particular, region 1402 includes some variation in R-wave amplitudes, and beats distributed as shown in within the 0.1 second R-R interval length bins between 1.5 and 2.4 seconds, with the greatest number of beats having R-R interval lengths between about 0.7 and 0.9 seconds. The pattern of R-R interval and R-wave amplitude value combinations associated with bradycardia may, as illustrated by region 1402, be dispersed or checkered and shifted towards larger R-R interval values (e.g., right in FIG. 16) relative to the normal data set illustrated by FIG. 15.

Figure 17:
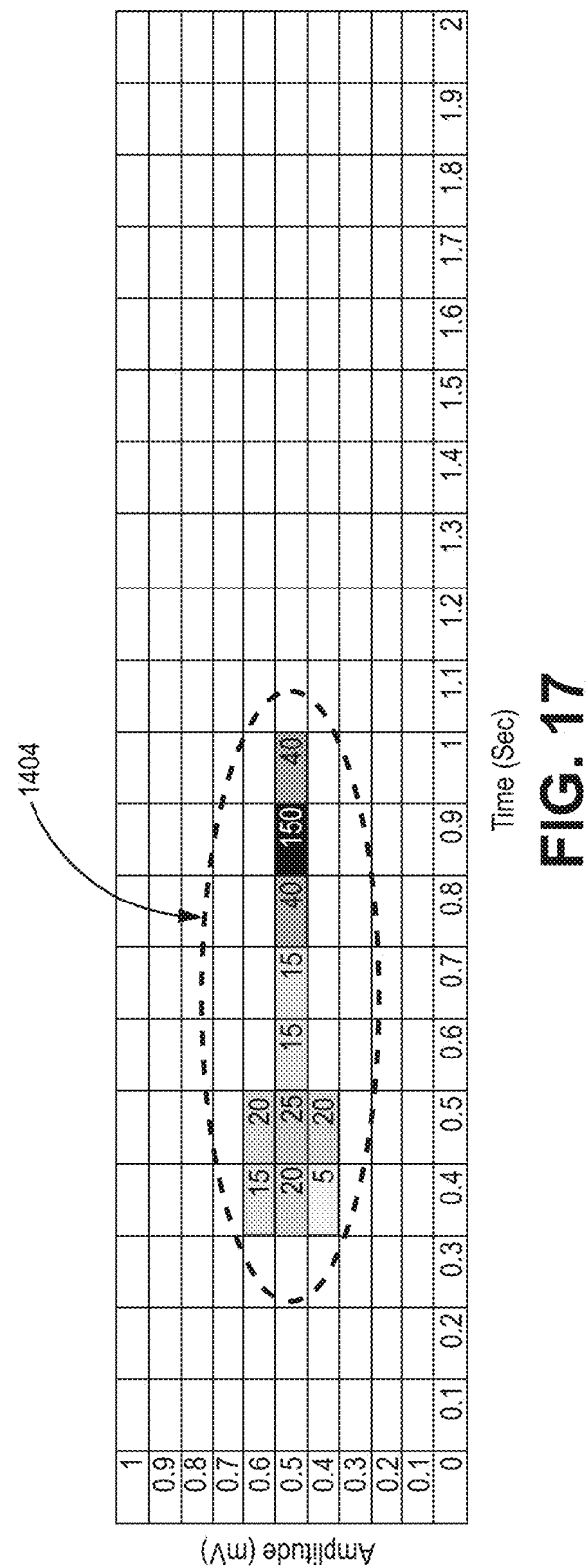

As another example, FIG. 17 is a heat map plot of occurrences of combinations of R-R interval and R-wave amplitude in a not normal data set and, more particularly, a data set that would be classified as tachyarrhythmia, e.g., treatable tachyarrhythmia, with each beat binned within one of the 0.1 mV amplitude bins between 0 and 1 mV and one of the 0.1 second R-R interval length bins between 0 and 2 seconds. Region 1404 illustrates the distribution of such values in a tachyarrhythmia data set. In particular, region 1404 includes significant variation in R-wave amplitudes between 0.3 and 0.6 mV, particularly at shorter R-R interval lengths, and a significant number of beats with R-R interval lengths between 0.3 and 0.5 seconds, in contrast to the normal data set of FIG. 15 with most beats having R-R interval lengths greater than 0.6 seconds. The pattern illustrated by FIG. 17 may be described as including a significant grouping of beats having shorter than normal R-R interval lengths and higher than normal R-wave amplitude variability, e.g., on the left side of the heat map of FIG. 17.

Although FIG. 17 illustrates a data set that would be classified as tachyarrhythmia generally, data sets may have distinguishing characteristics, e.g., evident in heat maps, that would allow classification of particular types of treatable or not treatable tachyarrhythmias, such as ventricular fibrillation, ventricular tachycardia, or supra-ventricular tachycardia. Different patterns of groupings of beats for such different tachyarrhythmias may be evident, for example, in heat maps that plot discrete variables derived from the ECG, such as R-R interval length and R-wave amplitude, relative to waveform morphological characteristics, such as slope, area under curve, or values from a transform or turning point algorithm.

Figure 18:
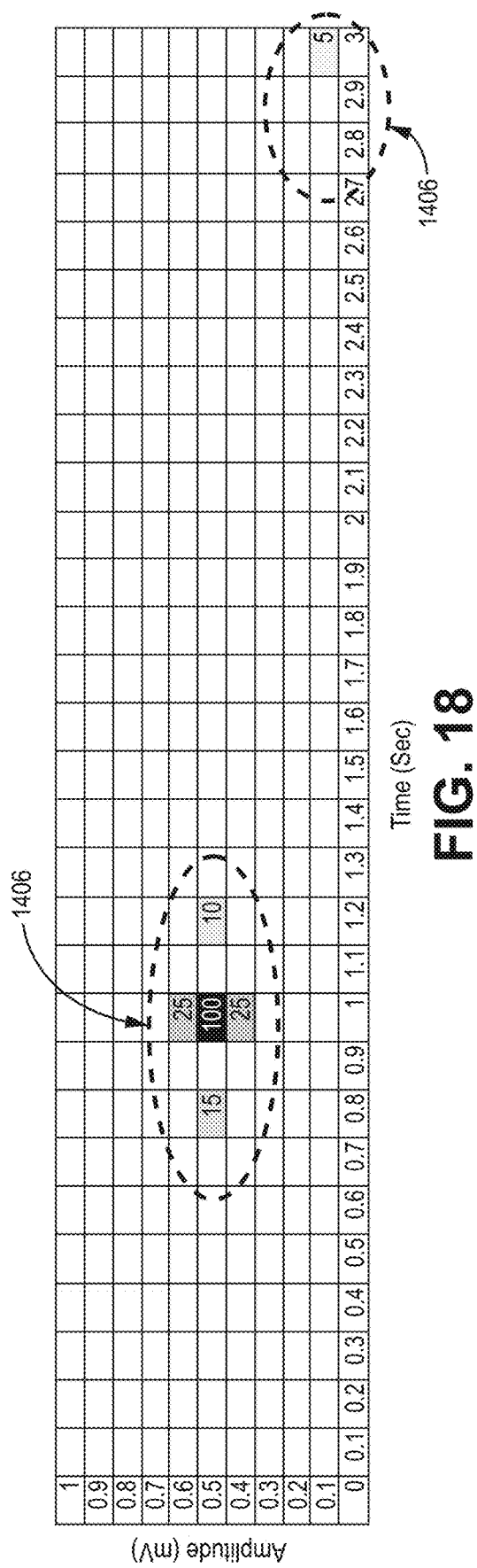

As another example, FIG. 18 is a heat map plot of occurrences of combinations of R-R interval and R-wave amplitude in a not normal data set and, more particularly, a data set that would be classified as syncope, which is characterized by sudden rate and amplitude variation followed by a flat line in the cardiac signal. In the example of FIG. 18, each beat is binned within one of the 0.1 mV amplitude bins between 0 and 1 mV and one of the 0.1 second R-R interval length bins between 0 and 3 seconds. Region 1406 illustrates the distribution of such values in a syncope data set. In particular, region 1406 includes significant variation in R-wave amplitudes, and two distinct clusters of beats respectively having R-R interval lengths between 0.7 and 1.2 seconds and greater than 2.9 seconds. The syncopal beats with significantly longer R-R interval lengths also have lower R-wave amplitudes.

Figure 19:
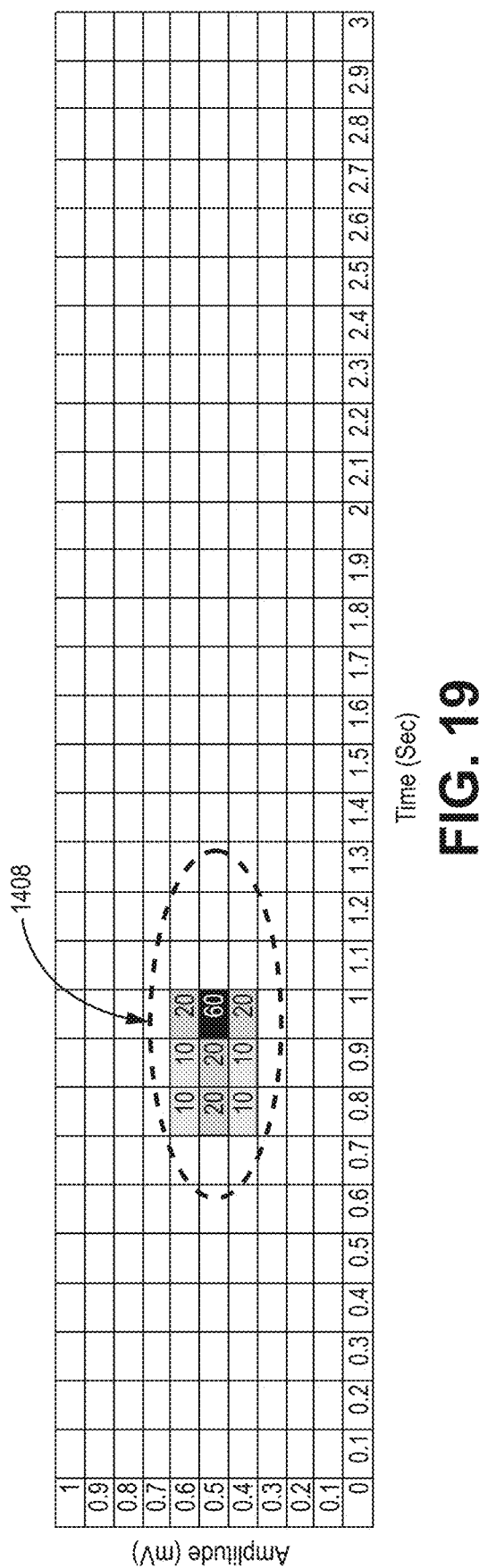

As another example, FIG. 19 is a heat map plot of occurrences of combinations of R-R interval and R-wave amplitude in a not normal data set and, more particularly, a data set that would be classified as 60 Hertz noise, which is characterized by a slight sine wave like variation in R-wave amplitude. In the example of FIG. 19, each beat is binned within one of the 0.1 mV amplitude bins between 0 and 1 mV and one of the 0.1 second R-R interval length bins between 0 and 3 seconds. Region 1408 illustrates the distribution of such values in a 60 Hertz noise data set, which is characterized by a pattern of greater R-wave amplitude variability than the normal data set of FIG. 15, but R-R interval lengths consistent with those of the normal data set.

Figure 20:
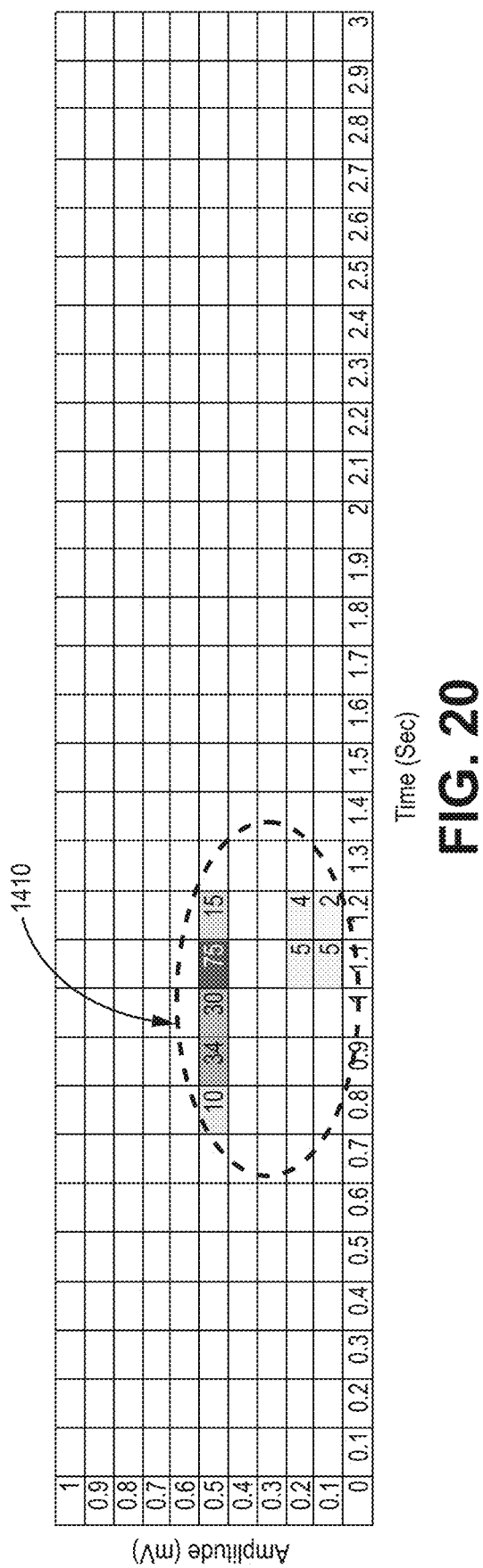

As another example, FIG. 20 is a heat map plot of occurrences of combinations of R-R interval and R-wave amplitude in a not normal data set and, more particularly, a data set that would be classified as signal loss, e.g., due to one or more electrodes failing, being removed, or otherwise becoming inoperable, which is characterized by noise associated with loss of and reconnection to the signal source. In the example of FIG. 20, each beat is binned within one of the 0.1 mV amplitude bins between 0 and 1 mV and one of the 0.1 second R-R interval length bins between 0 and 3 seconds. Region 1410 illustrates the distribution of such values in a signal loss data set, including distinct clusters of different R-wave amplitudes associated with loss and normal data, but R-R interval lengths consistent with those of the normal data set.

Figure 21:
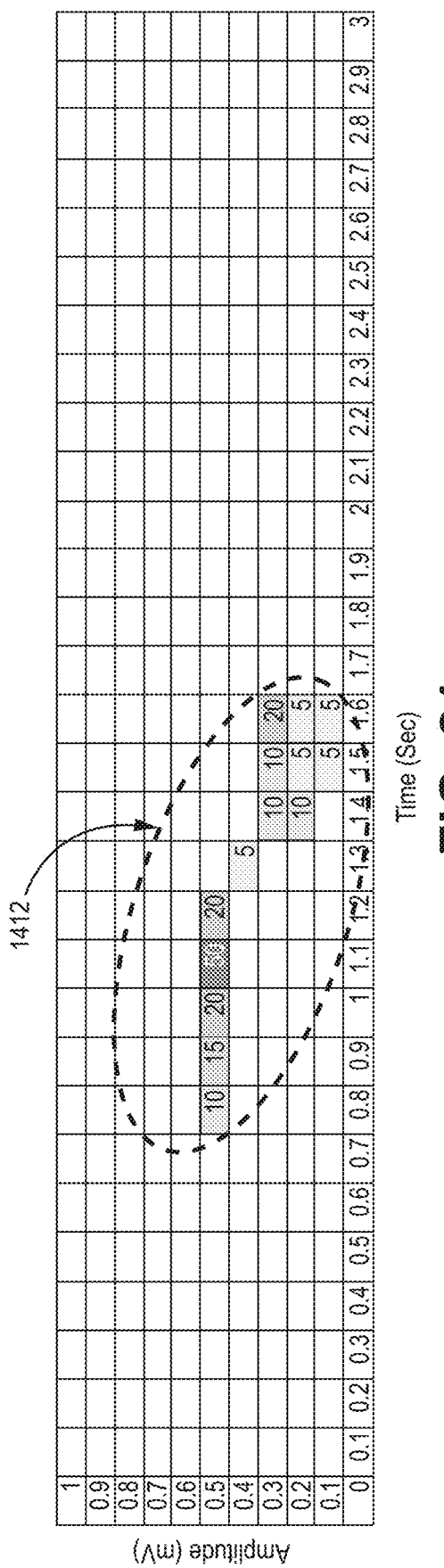

As another example, FIG. 21 is a heat map plot of occurrences of combinations of R-R interval and R-wave amplitude in a not normal data set and, more particularly, a data set that would be classified as electrode peeling off, which is characterized by gradual reduction in amplitude until signal loss. In the example of FIG. 21, each beat is binned within one of the 0.1 mV amplitude bins between 0 and 1 mV and one of the 0.1 second R-R interval length bins between 0 and 3 seconds. Region 1412 illustrates the distribution of such values in a signal loss data set, including a significant number of beats with lower R-wave amplitude and longer R-R interval lengths (e.g., due to missed beats) associated with signal loss.

Figure 22:
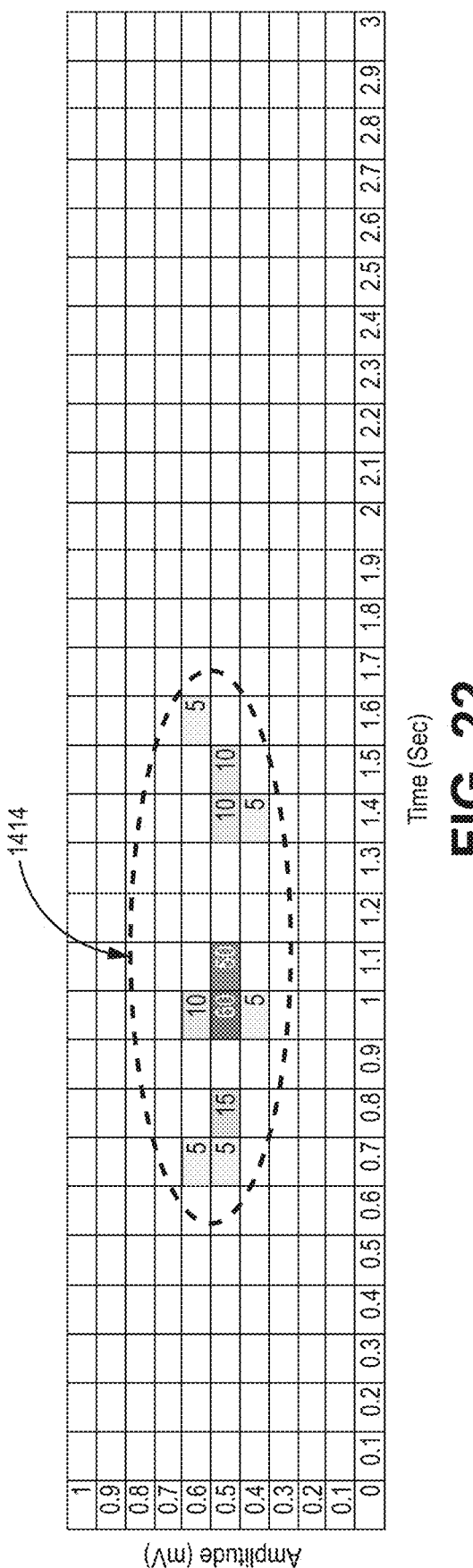

As another example, FIG. 22 is a heat map plot of occurrences of combinations of R-R interval and R-wave amplitude in a not normal data set and, more particularly, a data set that would be classified as R-R interval variability, e.g., due to atrial fibrillation. In the example of FIG. 22, each beat is binned within one of the 0.1 mV amplitude bins between 0 and 1 mV and one of the 0.1 second R-R interval length bins between 0 and 3 seconds. Region 1414 illustrates the distribution of such values in a R-R interval variability data set, including rapid and relatively large variation of the time interval between R-wave peaks and their amplitude, e.g., due to sporadic conduction of the rapid atrial depolarizations of atrial fibrillation. The pattern illustrated by region 1414 includes significant numbers of beats throughout a wider R-R interval range than the normal data set of FIG. 15.

Figure 23:
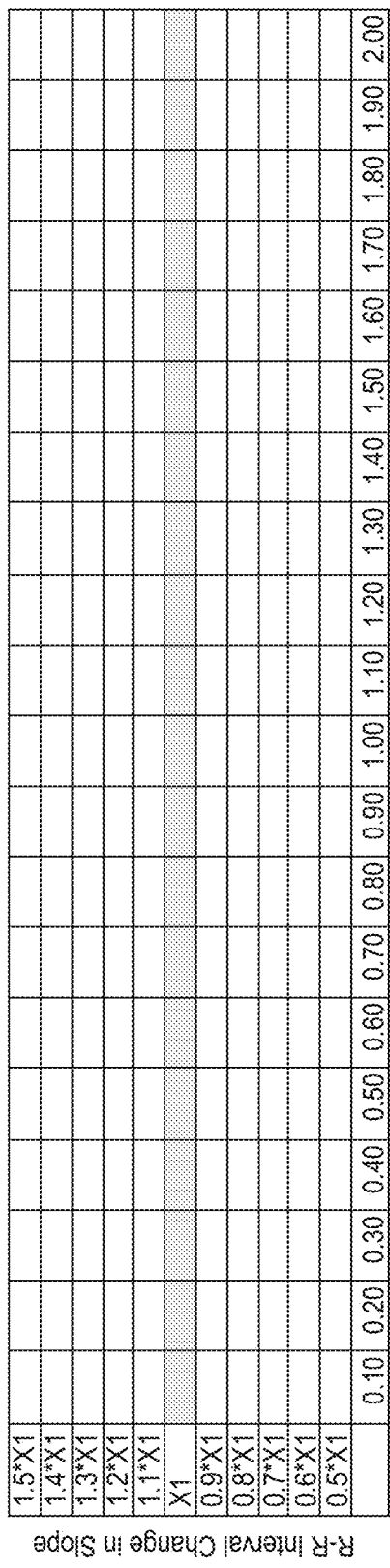
FIGS. 23 and 24 are diagrams illustrating R-R interval slope data that a machine learning algorithm would learn to classify as normal and not normal, respectively, according to examples of the techniques of this disclosure.
Figure 24:
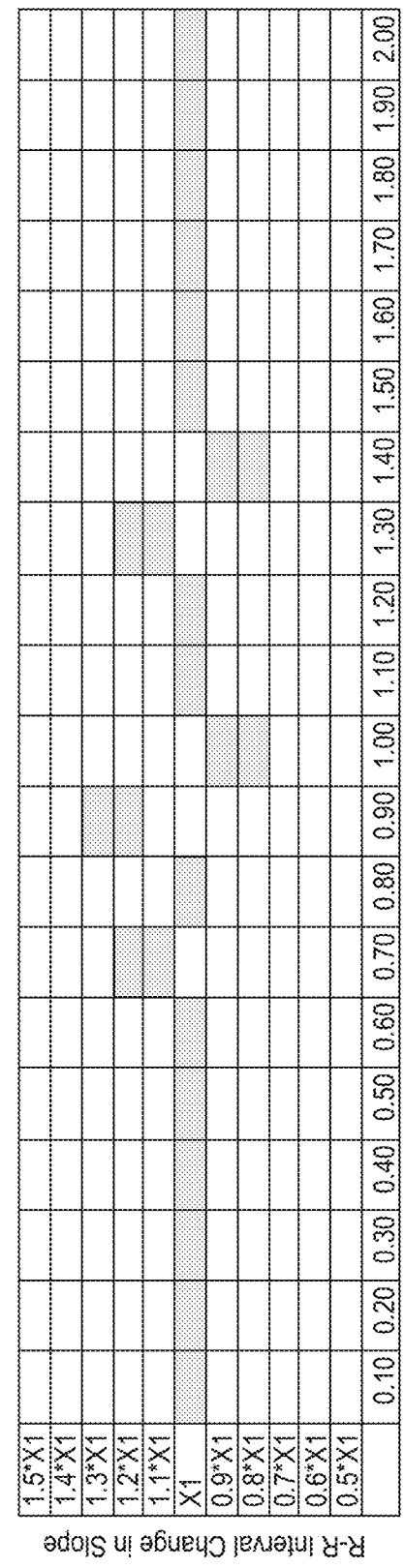

FIGS. 23 and 24 are diagrams illustrating R-R interval slope data that a machine learning algorithm would learn to classify as normal and not normal, respectively, according to examples of the techniques of this disclosure. In particular, FIGS. 23 and 24 illustrate R-R interval slope values measured for consecutive beats during a two-minute period, with each beat binned in the 0.1 minute bin in which it occurred, and the mean or median R-R interval having a length of X1. As illustrated in FIG. 23, the normal data set has consistent R-R interval slope values within 0.1*X1 range including X1. As illustrated in FIG. 24, the not normal data set includes significantly greater variation in R-R interval slope over time, with R-R interval values between 0.8*X1 and 1.4*X1.

Figure 25:
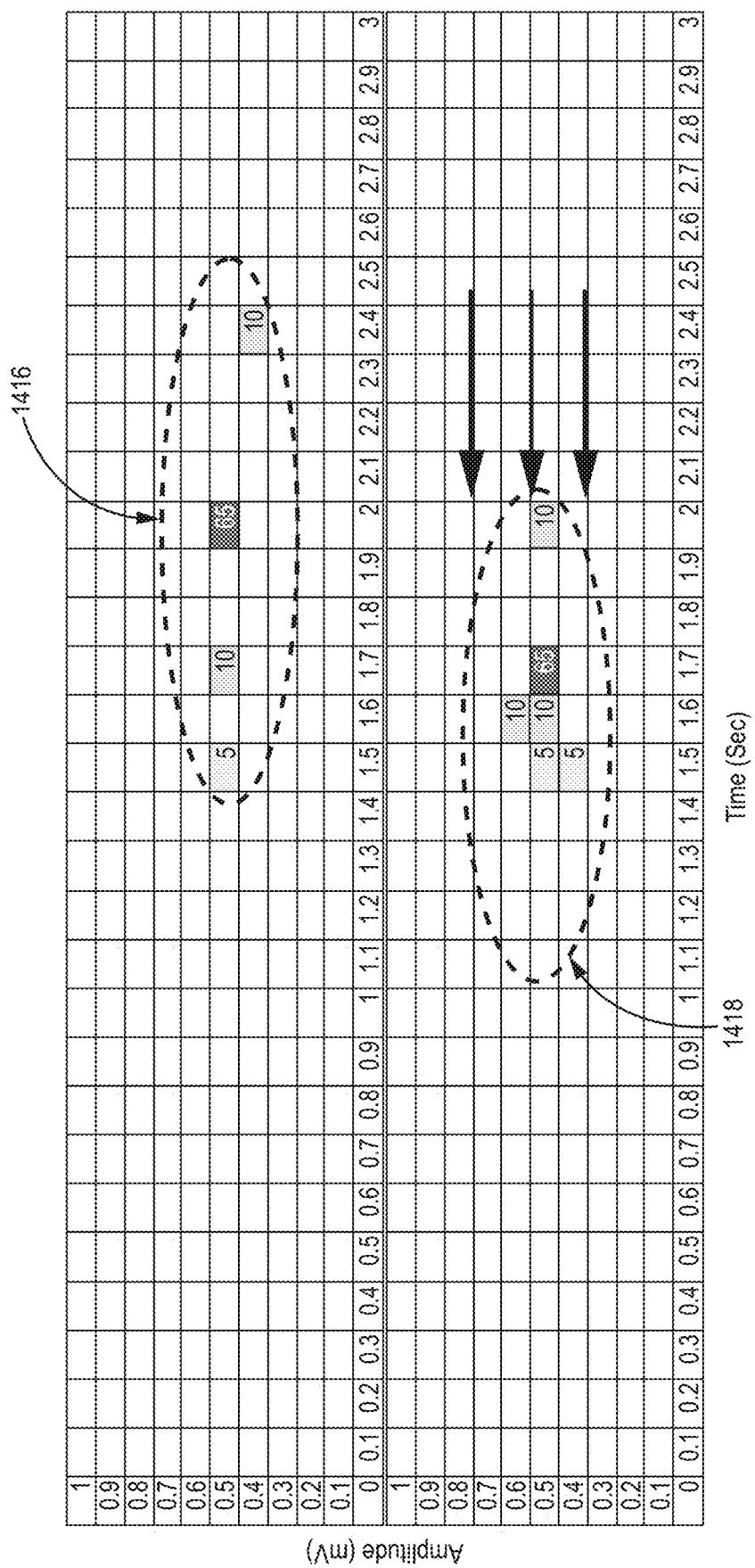
FIG. 25 is a diagram illustrating data from cardiac signals of patients in different populations that a machine learning algorithm would learn to classify as not normal according to examples of the techniques of this disclosure.

FIG. 25 is a diagram illustrating data from cardiac signals of patients in different populations that a machine learning algorithm would learn to classify as not normal according to examples of the techniques of this disclosure. In the example of FIG. 25, each beat is binned within one of the 0.1 mV amplitude bins between 0 and 1 mV and one of the 0.1 second R-R interval length bins between 0 and 3 seconds. More particularly, region 1416 illustrates the distribution of a bradycardia data set in a relatively younger patient, while region 1418 illustrates the distribution of a bradycardia data set in a relatively older, e.g., elderly, patient. With increase age, a slightly elevated resting heart rate is expected, and the bradycardia data for the older patient similarly includes shorter R-R intervals. Consistent with this expectation, the pattern of beats illustrated by region 1418 is shifted to shorter R-R intervals (e.g., left in FIG. 25) relative to region 1416. To account for these differences between patient populations, a machine learning algorithm may be adapted using data sets from patients in a population having characteristics matching the patient.

Figure 26:
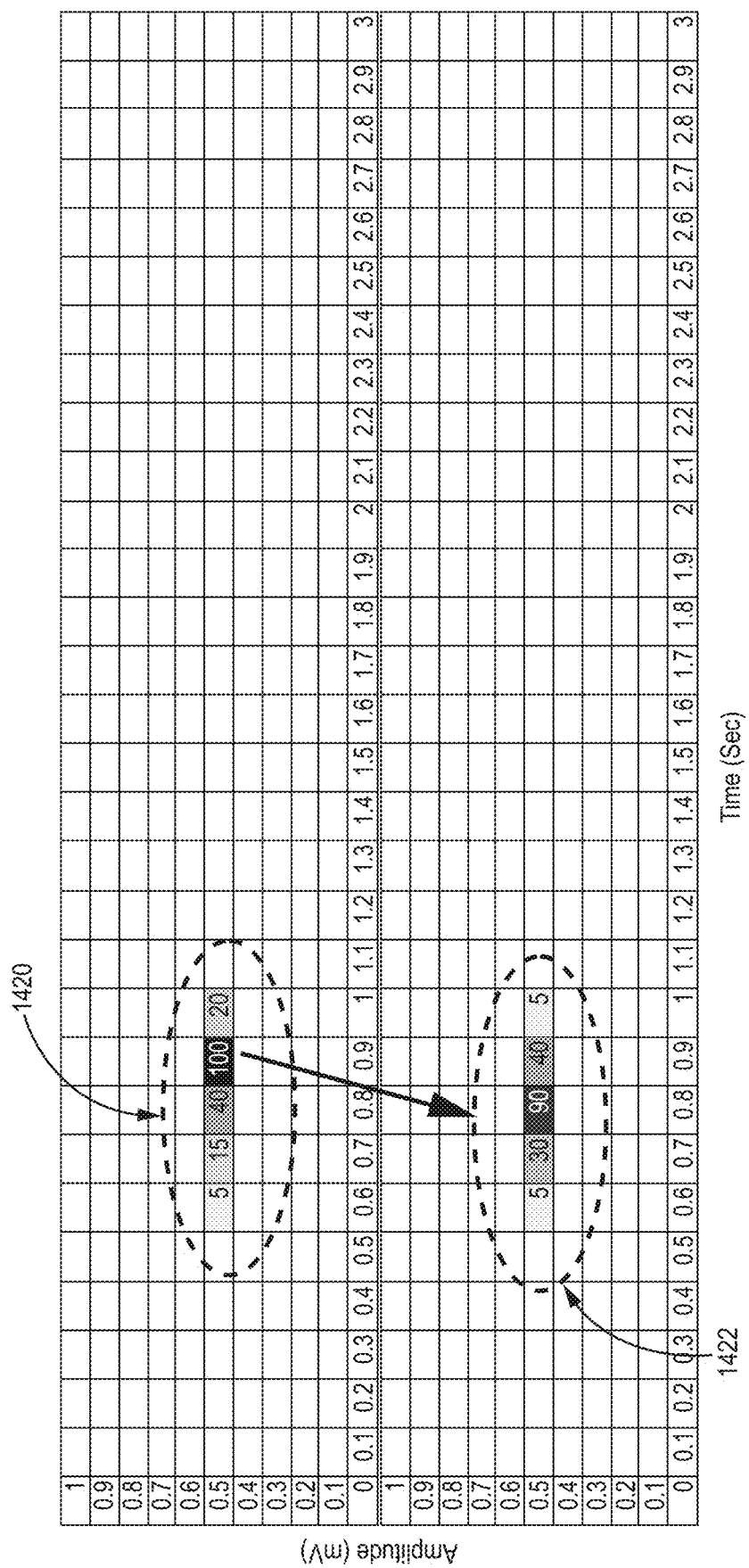
FIG. 26-28 are diagrams illustrating data form cardiac signals of patients in different populations that a machine learning algorithm would learn to classify as normal according to examples of the techniques of this disclosure.
Figure 27:
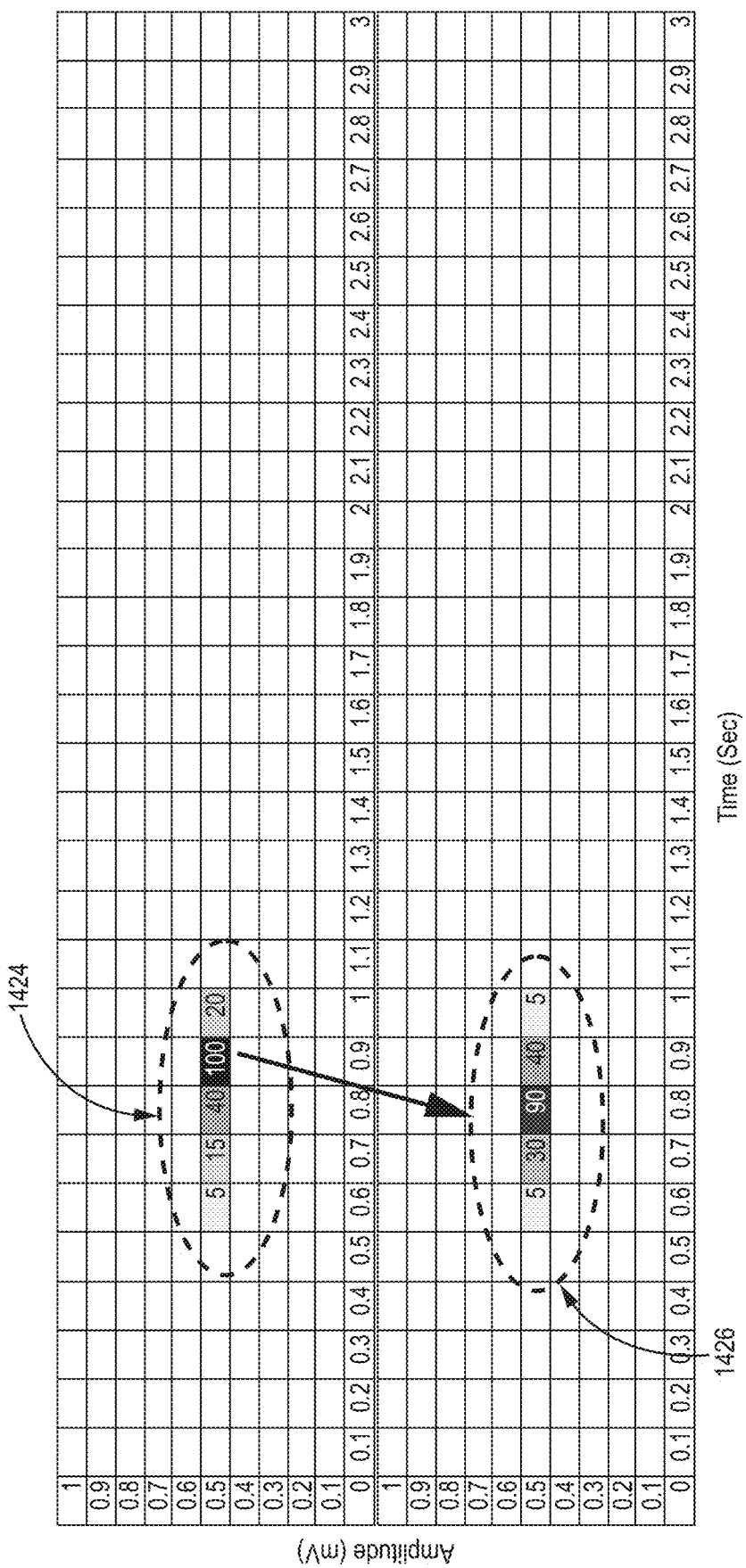
Figure 28:
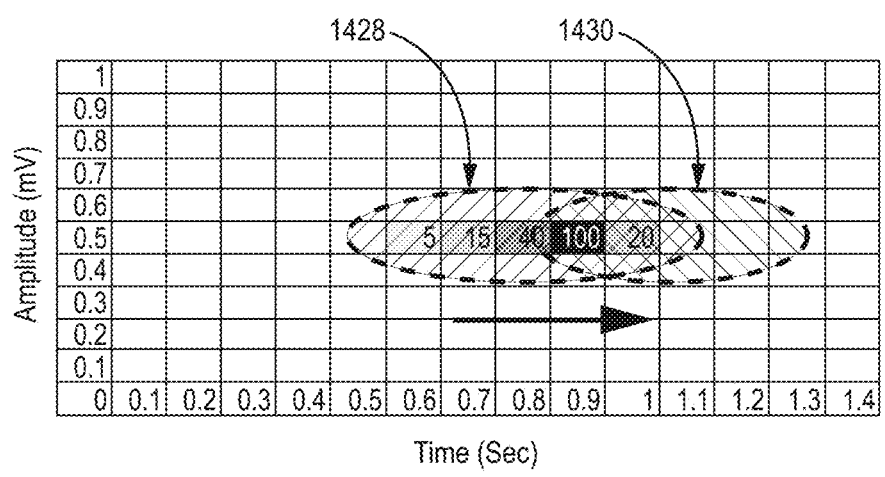

FIG. 26-28 are diagrams illustrating data form cardiac signals of patients in different populations that a machine learning algorithm would learn to classify as normal according to examples of the techniques of this disclosure. FIGS. 26-28 are heat map plots of occurrences of combinations of R-R interval and R-wave amplitude in the data. In the examples of FIGS. 26-28, each beat is binned within one of the 0.1 mV amplitude bins between 0 and 1 mV and one of the 0.1 second R-R interval length bins between 0 and 3 seconds (although FIG. 28 only illustrates the portion of the heat map from 0 to 1.4 seconds).

For example, region 1420 of FIG. 26 illustrates the distribution of data for an average or normal BMI patient, while region 1422 illustrates the distribution of the data for an increased BMI patient. Increased resting heart rate is expected with increased BMI, which is reflected in the, e.g., about 0.1 second, relative shift in the location of the most populous value combination between regions 1420 and 1422. In particular, region 1420 includes 100 beats with an R-R interval within a range from about 0.8 seconds to about 0.9 seconds, while region 1422 includes 90 beats with an R-R interval within a range from about 0.7 second to about 0.8 seconds. Similarly, regions 1424 and 1426 in FIG. 27 illustrate the data distributions for a male and female, respectively, with females expected to have about a 5-10 bpm greater resting rate than males. Also, FIG. 28 illustrates data in region 1428 that would be expected from a patient having higher blood pressure. FIG. 28 also illustrates region 1430 where it would be expected that data of a patient having lower blood pressure would occur in the heat map. In this manner, FIG. 28 illustrates how increased blood pressure relates to increased heart rate, and how each are co-factors for the other. Again, to account for these differences between patient populations, a machine learning algorithm may be adapted using data sets from patients in a population having characteristics matching the patient. The characteristics that may distinguish patient populations include gender, age, BMI, weight, and blood pressure. Further, the machine learning algorithm may use the expected difference in data illustrated by regions 1428 and 1428 to determine the state of a comorbidity related to blood pressure for a patient.

Figure 29:
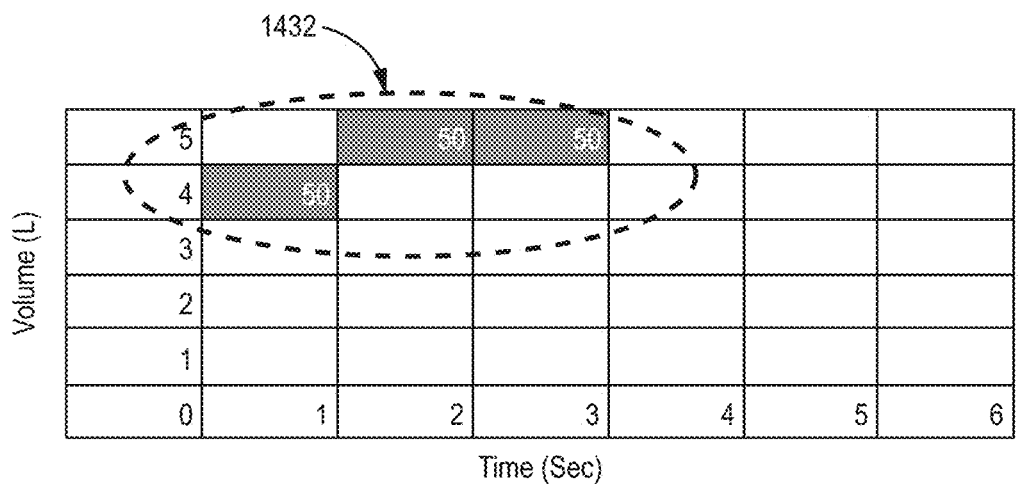
FIG. 29 is a diagram illustrating data from a spirometer signal of a patient that a machine learning algorithm would learn to classify as normal according to examples of the techniques of this disclosure.

FIG. 29 is a diagram illustrating data from a spirometer signal of a patient that a machine learning algorithm would learn to classify as normal according to examples of the techniques of this disclosure. In particular, FIG. 29 illustrates a heat map of values of volume over time during exhalation into a spirometer. Region 1432 illustrates a distribution of such values that would be classified as normal.

Values that may be determined from a spirometer signal include forced exhalation volume in one second (FEV1) and forced vital capacity (FVC), which is the amount of air which can be forcibly exhaled from the lungs after taking the deepest breath possible. FVC is essentially equivalent lung capacity, and may be calculated as an integral or area under the curve of a signal from a spirometer during such an exhalation. FEV1 may similarly be calculated, but based only on the first second of the signal. The ratio of FEV1 to FVC may also be determined. Normal values for these parameters are FEV1 and FVC greater than 80%, and FEV1/FVC greater than 70%.

Figure 30:
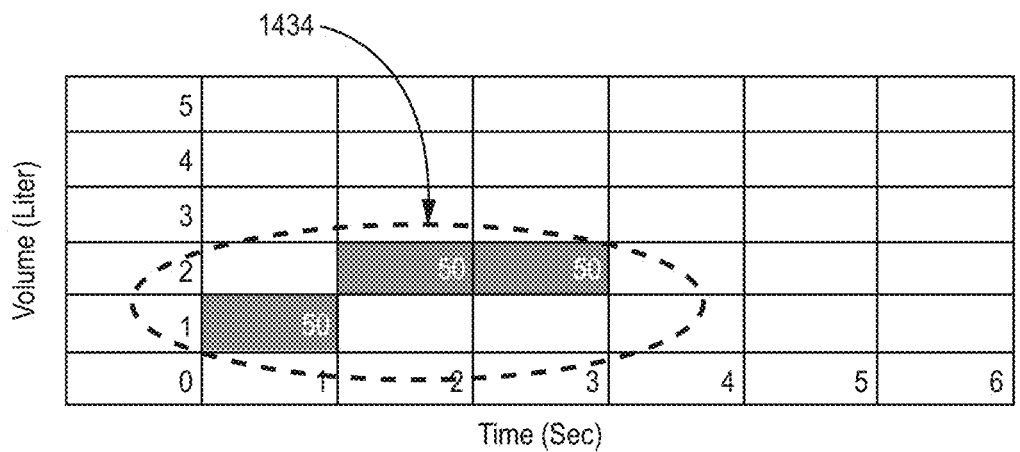
FIG. 30 is a diagram illustrating data from a spirometer signal of a patient that a machine learning algorithm would learn to classify as not normal according to examples of the techniques of this disclosure.

FIG. 30 is a diagram illustrating data from a spirometer signal of a patient that a machine learning algorithm would learn to classify as not normal according to examples of the techniques of this disclosure. In particular, FIG. 30 illustrates a heat map of the values of volume over time during exhalation into a spirometer. Region 1434 illustrates a distribution of such values that would be classified as not normal. The distribution of region 1434 includes lower volume values than region 1432 of FIG. 29, and correlates to an FVC of about 35% and an FEV1 of about 20%, with a ratio of about 50%. Generally, COPD will demonstrate reduced FEV1 and FVC below 80%, and FEV1/FVC below 70%.

Figure 31:
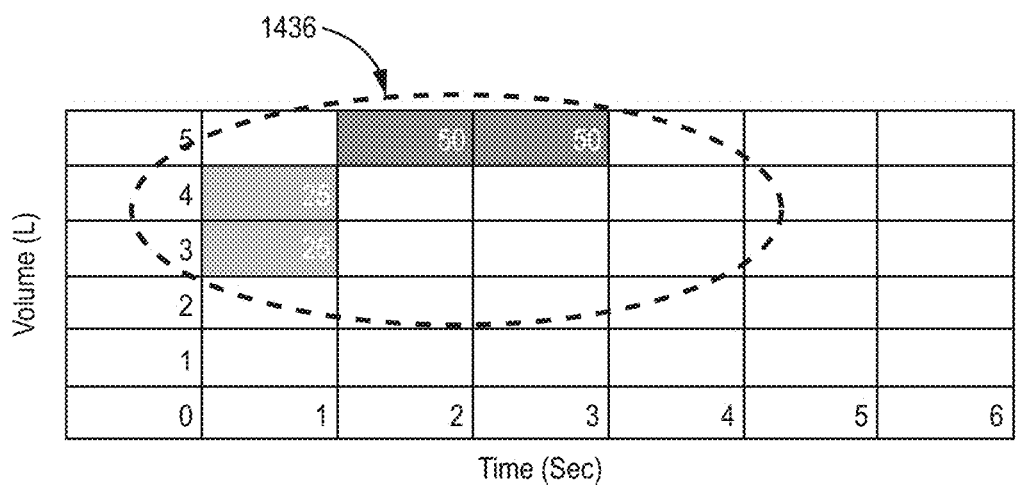
FIG. 31 is a diagram illustrating data from a spirometer signal of an elderly patient that a machine learning algorithm would learn to classify as normal according to examples of the techniques of this disclosure.

FIG. 31 is a diagram illustrating data from a spirometer signal of an elderly patient that a machine learning algorithm would learn to classify as normal according to examples of the techniques of this disclosure. In particular, FIG. 31 illustrates a heat map of values of volume over time during exhalation into a spirometer. Region 1436 illustrates a distribution of such values that would be classified as normal in an elderly patient. The distribution of region 1436 correlates to an FEV1/FVC ratio of about 65%. To account for such differences in spirometer difference between populations with different characteristics, such as age, a machine learning algorithm for classifying COPD may be adapted based on population-specific data sets, as described herein.

Figure 32:
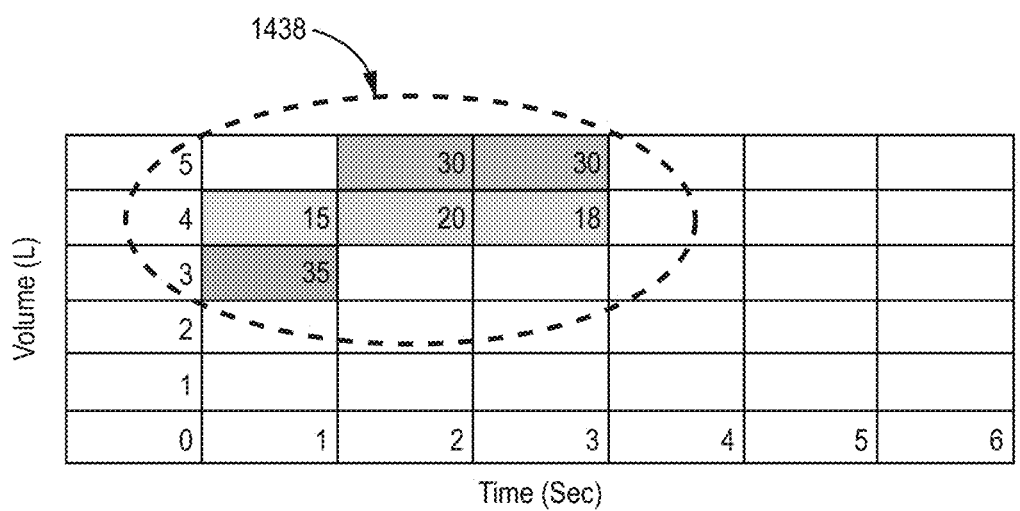
FIG. 32 is a diagram illustrating data form spirometer signals in varying air quality conditions.

FIG. 32 is a diagram illustrating data form spirometer signals in varying air quality conditions, e.g., with varying air particle counts. Certain ranges of particle counts are unhealthy for sensitive patients, such as those with COPD, while particle counts above this range are necessary to be considered unhealthy for an otherwise healthy patient. Generally, though, increased particle count may have an impact on lung volume of a normal person, as well as correlating with COPD. Region 1438 illustrates a distribution of spirometer data with fluctuating particle count, characterized by greater variance and rapid changes. Fluctuations in particle count may correlate to fluctuations in FEV1, FVC, and FEV1/FVC. A machine learning algorithm for classifying COPD may consider particle count with other data, such as spirometer data, to account for such fluctuations.

In some examples, machine learning as described herein, is an aspect of artificial intelligence. The systems and techniques described herein may include artificial intelligence, which includes reasoning, natural language processing, machine learning, and planning. In general machine learning may include iterative learning cycles, such as supervised learning, unsupervised learning, reinforced learning, and deep learning networks.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other non-transitory computer readable media.

Various aspects of the disclosure have been described. These and other aspects are within the scope of the following claims.

What is claimed is:

1. An apparatus configured to be worn by a patient for cardiac defibrillation, the apparatus comprising:
   sensing electrodes configured to sense a cardiac signal of the patient;
   defibrillation electrodes;
   therapy delivery circuitry configured to deliver defibrillation therapy to the patient via the defibrillation electrodes;
   communication circuitry configured to receive data of at least one physiological signal of the patient from at least one sensing device separate from the apparatus;
   a memory configured to store the data of the at least one physiological signal, the cardiac signal, and a machine learning algorithm; and
   processing circuitry configured to:
      apply the machine learning algorithm to the cardiac signal to probabilistically determine a preliminary characterization of at least one state of the patient;
      determine, based on the machine learning algorithm being applied to the cardiac signal, the preliminary characterization of at least one state of the patient is not normal;
      apply, based on the preliminary characterization being not normal, the machine learning algorithm to both the data of the at least one physiological signal and the cardiac signal to probabilistically determine the at least one state of the patient; and
      determine whether to control delivery of the defibrillation therapy based on the at least one probabilistically-determined state of the patient,
      wherein the machine learning algorithm is configured to automatically update itself based on at least one of the data of the at least one physiological signal or the cardiac signal.

2. The apparatus of claim 1, wherein the at least one sensing device comprises a subcutaneously implantable cardiac monitor comprising a plurality of sensing electrodes to sense the physiological signal, wherein the cardiac signal comprises a first cardiac signal and the physiological signal comprises a second cardiac signal.

3. The apparatus of claim 1, wherein the machine learning algorithm is configured to automatically update itself based on input from at least one of the patient or a healthcare provider.

4. The apparatus of claim 1, wherein the data of the physiological signal comprises a determination, by the sensing device, of whether a tachyarrhythmia is indicated by the physiological signal, wherein the machine learning algorithm is configured to automatically update itself based on the determination by the sensing device.

5. The apparatus of claim 1, wherein the at least one sensing device comprises at least one of:
   a glucose monitor, wherein the physiological signal comprises a glucose concentration in the patient;
   an electroencephalography (EEG) sensor, wherein the physiological signal comprises brain activity;
   a pressure monitoring device, wherein the physiological signal comprises a cardiovascular pressure signal;
   a pulse oximetry device, wherein the physiological signal comprises at least one of pulse rate, oxygen saturation, or respiration rate;
   a patient activity tracker, wherein the physiological signal comprises physical activity of the patient; or
   a location tracker configured to determine a location of the patient.

6. The apparatus of claim 5,
wherein the at least one sensing device comprises the patient activity tracker, and
wherein the patient activity tracker comprises a wearable sensing device configured to be worn on the patient.

7. The apparatus of claim 1, wherein the apparatus comprises a wearable automated external defibrillator (WAED) comprising a garment configured to be worn by the patient, wherein the sensing electrodes and defibrillation electrodes are coupled to the garment.

8. The apparatus of claim 1, wherein inputs to the machine learning algorithm from the cardiac signal include one or more of an R-R interval, an amplitude of an R wave, a QRS width, or an R-R interval variability.

9. The apparatus of claim 1, wherein inputs to the machine learning algorithm from the cardiac signal and the data of the at least one physiological signal comprises one or more of a size of a feature of the signal, a frequency of the feature, a morphology of the feature, or a change in the size, frequency, or morphology over time.

10. The apparatus of claim 1, wherein the processing circuitry is configured to control the therapy delivery circuitry to deliver the defibrillation therapy based on a result of the application of the machine learning algorithm to the data of the at least one physiological signal and the cardiac signal.

11. The apparatus of claim 1, wherein the processing circuitry comprises a graphics processing unit (GPU) configured to apply the machine learning algorithm to the data of the at least one physiological signal and the cardiac signal to probabilistically determine the at least one state of the patient.

12. The apparatus of claim 1, wherein the at least one probabilistically- determined patient state comprises at least one of:
whether the patient state normal; or
whether the patient state is treatable tachyarrhythmia.

13. The apparatus of claim 12, wherein a probabilistically-determined patient state of not normal further comprises a sub-classification of one of bradycardia, treatable tachyarrhythmia, syncope, 60 Hertz noise, motion artifacts, or loss of signal.

14. The apparatus of claim 12, wherein the at least one probabilistically-determined patient state comprises a predicted treatable tachyarrhythmia patient state, the therapy delivery circuitry is configured to deliver a therapy configured to prevent tachyarrhythmia, and the processing circuitry is further configured to determine whether to deliver the therapy configured to prevent tachyarrhythmia based on the predicted treatable tachyarrhythmia state.

15. The apparatus of claim 12, wherein the at least one probabilistically-determined patient state comprises at least one comorbidity state of the patient.

16. The apparatus of claim 15, wherein the at least one comorbidity state of the patient comprises a COPD state of the patient, and the at least one sensing device comprises:
a spirometer configured to generate a spirometer signal; and
an air quality sensor configured to generate an air quality signal,
wherein the processing circuitry is further configured to determine the COPD state of the patient based on application of the machine learning algorithm to the spirometer signal and the air quality signal.

17. The apparatus of claim 15, wherein, based on the at least one comorbidity state of the patient, the processing circuitry is configured to provide an instruction to the patient.

18. A method for monitoring cardiac signals and determining whether to deliver defibrillation therapy by apparatus configured to be worn by a patient, the method comprising:
sensing, via sensing electrodes of the apparatus, a cardiac signal of the patient;
receiving, by communication circuitry of the apparatus, data of at least one physiological signal of the patient from at least one sensing device separate from the apparatus;
storing, by a memory of the apparatus, the cardiac signal, the data of the at least one physiological signal, and a machine learning algorithm;
applying, by processing circuitry of the apparatus, the machine learning algorithm to the data of the cardiac signal to probabilistically determine a preliminary characterization of at least one state of the patient;
determining, by processing circuitry of the apparatus and based on the machine learning algorithm being applied to the cardiac signal, the preliminary characterization of at least one state of the patient is not normal;
applying, by the processing circuitry of the apparatus and based on the preliminary characterization being not normal, the machine learning algorithm to both the data of the at least one physiological signal and the cardiac signal to probabilistically determine the at least one state of the patient;
determining, by the processing circuitry, whether to control delivery of defibrillation therapy by therapy delivery circuitry of the apparatus based on the at least one probabilistically-determined state of the patient, and
automatically updating the machine learning algorithm based on at least one of the data of the at least one physiological signal or the cardiac signal.

19. The method of claim 18, wherein the at least one sensing device comprises a subcutaneously implantable cardiac monitor comprising a plurality of sensing electrodes to sense the physiological signal, wherein the cardiac signal comprises a first cardiac signal and the physiological signal comprises a second cardiac signal.

20. The method of claim 18, wherein the machine learning algorithm is configured to automatically update itself based on input from at least one of the patient or a healthcare provider.

21. The method of claim 18, wherein the data of the physiological signal comprises a determination, by the sensing device, of whether a tachyarrhythmia is indicated by the physiological signal, wherein the machine learning algorithm is configured to automatically update itself based on the determination by the sensing device.

22. The method of claim 18, wherein the at least one sensing device comprises at least one of:
a glucose monitor, wherein the physiological signal comprises a glucose concentration in the patient;
an electroencephalography (EEG) sensor, wherein the physiological signal comprises brain activity;
a pressure monitoring device, wherein the physiological signal comprises a cardiovascular pressure signal;
a pulse oximetry device, wherein the physiological signal comprises at least one of pulse rate, oxygen saturation, or respiration rate;
a patient activity tracker, wherein the physiological signal comprises physical activity of the patient; or a location tracker configured to determine a location of the patient.

23. The method of claim 18, wherein the apparatus comprises a wearable automated external defibrillator (WAED) comprising a garment configured to be worn by the patient, wherein the sensing electrodes and defibrillation electrodes are coupled to the garment.

24. The method of claim 18, wherein inputs to the machine learning algorithm from the cardiac signal include one or more of an R-R interval, an amplitude of an R wave, a QRS width, or an R-R interval variability.

25. The method of claim 18, wherein inputs to the machine learning algorithm from the cardiac signal and the data of the at least one physiological signal comprises one or more of a size of a feature of the signal, a frequency of the feature, a morphology of the feature, or a change in the size, frequency, or morphology over time.

26. The method of claim 18, wherein the therapy delivery circuitry is configured to deliver a therapy configured to prevent tachyarrhythmia, and the processing circuitry is further configured to determine whether to deliver the therapy configured to prevent tachyarrhythmia based on the application of the machine learning algorithm to the cardiac signal and the physiological signal.

27. The method of claim 18, further comprising controlling, by the processing circuitry the delivery of the defibrillation therapy based on a result of the application of the machine learning algorithm to the data and the cardiac signal.

28. The method of claim 18, wherein the processing circuitry of the apparatus comprises a graphics processing unit (GPU) configured to apply the machine learning algorithm to the data and the cardiac signal to probabilistically determine the at least one state of the patient.

29. The method of claim 18, wherein the at least one probabilistically- determined patient state comprises at least one of:
   whether the patient state normal; or
   whether the patient state is treatable tachyarrhythmia.

30. The method of claim 29, wherein a probabilistically-determined patient state of not normal further comprises a sub-classification of one of bradycardia, treatable tachyarrhythmia, syncope, 60 Hertz noise, motion artifacts, or loss of signal.

31. The method of claim 29, wherein the at least one probabilistically-determined patient state comprises a predicted tachyarrhythmia patient state, the therapy delivery circuitry is configured to deliver a therapy configured to prevent tachyarrhythmia, and the processing circuitry is further configured to determine whether to deliver the therapy configured to prevent tachyarrhythmia based on the predicted tachyarrhythmia state.

32. The method of claim 29, wherein the at least one probabilistically-determined patient state comprises at least one comorbidity state of the patient.

33. The method of claim 32, wherein the at least one comorbidity state of the patient comprises a COPD state of the patient, and the at least one sensing device comprises:
   a spirometer configured to generate a spirometer signal; and
   an air quality sensor configured to generate an air quality signal,
   wherein the processing circuitry is further configured to determine the COPD state of the patient based on application of the machine learning algorithm to the spirometer signal and the air quality signal.

34. The method of claim 32, wherein, based on the at least one comorbidity state of the patient, the processing circuitry is configured to provide an instruction to the patient.

* * * * *